US011272925B2

(12) United States Patent
Gittings et al.

(10) Patent No.: US 11,272,925 B2
(45) Date of Patent: Mar. 15, 2022

(54) METHODS AND DEVICES FOR SUTURE ANCHOR DELIVERY

(71) Applicant: The Foundry, LLC, Menlo Park, CA (US)

(72) Inventors: Darin C. Gittings, Sunnyvale, CA (US); Mark Deem, Mountain View, CA (US); Hanson S. Gifford, Woodside, CA (US); Doug Sutton, Pacifica, CA (US); Vivek Shenoy, Redwood City, CA (US)

(73) Assignee: THE FOUNDRY, LLC, Menlo Park, CA (US)

( * ) Notice: Subject to any disclaimer, the term of this patent is extended or adjusted under 35 U.S.C. 154(b) by 416 days.

(21) Appl. No.: 16/543,801

(22) Filed: Aug. 19, 2019

(65) Prior Publication Data
US 2019/0374222 A1    Dec. 12, 2019

Related U.S. Application Data

(60) Continuation of application No. 14/804,178, filed on Jul. 20, 2015, now Pat. No. 10,383,624, which is a
(Continued)

(51) Int. Cl.
*A61B 17/064* (2006.01)
*A61B 17/04* (2006.01)
*A61B 17/00* (2006.01)

(52) U.S. Cl.
CPC ...... *A61B 17/0642* (2013.01); *A61B 17/0401* (2013.01); *A61B 2017/00398* (2013.01);
(Continued)

(58) Field of Classification Search
CPC ............ A61B 17/0401; A61B 17/0642; A61B 2017/00398; A61B 2017/00411;
(Continued)

(56) References Cited

U.S. PATENT DOCUMENTS 3,939,969 A    2/1976 Miller et al.
3,981,307 A    9/1976 Borysko
(Continued)

FOREIGN PATENT DOCUMENTS

EP    1013229 A2    6/2000
EP    1588666 A2    10/2005
(Continued)

OTHER PUBLICATIONS

US 6,238,418 B1, 05/2001, Schwartz et al. (withdrawn)
(Continued)

*Primary Examiner* — Phong Son H Dang
(74) *Attorney, Agent, or Firm* — Wilson Sonsini Goodrich & Rosati

(57) ABSTRACT

A method for impacting a suture anchor into bone comprises providing an implantable suture anchor and providing an impactor device for impacting the suture anchor into the bone. The suture anchor is coupled to a distal portion of the impactor device. Positioning the suture anchor engages the anchor with the bone at an implantation site, and powering the impactor device impacts the suture anchor thereby implanting the suture anchor into the bone. The frequency of impaction is less than 20 KHz. The impactor device is then decoupled from the suture anchor, and the impactor device may be removed from the implantation site.

17 Claims, 8 Drawing Sheets

Related U.S. Application Data division of application No. 13/692,596, filed on Dec. 3, 2012, now abandoned, which is a continuation of application No. 12/605,065, filed on Oct. 23, 2009, now abandoned.

(60) Provisional application No. 61/108,420, filed on Oct. 24, 2008.

(52) U.S. Cl.
CPC ........... *A61B 2017/00411* (2013.01); *A61B 2017/00544* (2013.01); *A61B 2017/00867* (2013.01); *A61B 2017/00986* (2013.01); *A61B 2017/0409* (2013.01); *A61B 2017/0414* (2013.01); *A61B 2017/0432* (2013.01); *A61B 2017/0437* (2013.01)

(58) Field of Classification Search
CPC ........... A61B 2017/00544; A61B 2017/00867; A61B 2017/0409; A61B 2017/0414; A61B 2017/0432; A61B 2017/0437; A61B 2017/00986
See application file for complete search history.

(56) References Cited

U.S. PATENT DOCUMENTS

| | | | |
|---|---|---|---|
| 4,249,656 A | 2/1981 | Cerwin et al. |
| 4,253,563 A | 3/1981 | Komarnycky |
| 4,406,363 A | 9/1983 | Aday |
| 4,412,614 A | 11/1983 | Ivanov et al. |
| 4,413,727 A | 11/1983 | Cerwin et al. |
| 4,427,109 A | 1/1984 | Roshdy |
| 4,483,437 A | 11/1984 | Cerwin et al. |
| 4,491,218 A | 1/1985 | Aday |
| 4,533,041 A | 8/1985 | Aday et al. |
| 4,555,016 A | 11/1985 | Aday et al. |
| 4,572,363 A | 2/1986 | Alpern |
| 4,608,019 A | 8/1986 | Kumabe et al. |
| 4,615,435 A | 10/1986 | Alpern et al. |
| 4,750,492 A | 6/1988 | Jacobs |
| 4,884,681 A | 12/1989 | Roshdy et al. |
| 4,887,710 A | 12/1989 | Roshdy et al. |
| 4,898,156 A | 2/1990 | Gatturna et al. |
| 4,899,743 A | 2/1990 | Nicholson et al. |
| 4,904,272 A | 2/1990 | Middleton et al. |
| 4,946,043 A | 8/1990 | Roshdy et al. |
| 4,946,468 A | 8/1990 | Li |
| 4,968,315 A | 11/1990 | Gatturna |
| 4,969,892 A | 11/1990 | Burton et al. |
| 4,979,956 A | 12/1990 | Silvestrini |
| 5,002,550 A | 3/1991 | Li |
| 5,013,316 A | 5/1991 | Goble et al. |
| 5,019,083 A | 5/1991 | Klapper et al. |
| 5,046,513 A | 9/1991 | Gatturna et al. |
| 5,057,112 A | 10/1991 | Sherman et al. |
| 5,061,283 A | 10/1991 | Silvestrini |
| 5,078,730 A | 1/1992 | Li et al. |
| 5,108,400 A | 4/1992 | Appel et al. |
| 5,152,790 A | 10/1992 | Rosenberg et al. |
| 5,171,251 A | 12/1992 | Bregen et al. |
| 5,174,087 A | 12/1992 | Bruno |
| 5,178,629 A | 1/1993 | Kammerer |
| 5,188,636 A | 2/1993 | Fedotov |
| 5,192,303 A | 3/1993 | Gatturna et al. |
| 5,201,656 A | 4/1993 | Sicurelli, Jr. |
| 5,203,864 A | 4/1993 | Phillips |
| 5,207,679 A | 5/1993 | Li |
| 5,217,092 A | 6/1993 | Potter |
| 5,217,486 A | 6/1993 | Rice et al. |
| 5,242,457 A | 9/1993 | Akopov et al. |
| 5,258,016 A | 11/1993 | Dipoto et al. |
| 5,259,398 A | 11/1993 | Vrespa |
| 5,268,001 A | 12/1993 | Nicholson et al. |
| 5,282,809 A | 2/1994 | Kammerer et al. |
| 5,318,570 A | 6/1994 | Hood et al. |
| 5,336,240 A | 8/1994 | Metzler et al. |
| 5,352,230 A | 10/1994 | Hood |
| 5,358,511 A | 10/1994 | Gatturna et al. |
| 5,370,662 A | 12/1994 | Stone et al. |
| 5,380,334 A | 1/1995 | Torrie et al. |
| 5,383,905 A | 1/1995 | Golds et al. |
| 5,397,357 A | 3/1995 | Schmieding et al. |
| 5,407,420 A | 4/1995 | Bastyr et al. |
| 5,411,506 A | 5/1995 | Goble et al. |
| 5,411,523 A | 5/1995 | Goble |
| 5,415,651 A | 5/1995 | Schmieding |
| 5,417,691 A | 5/1995 | Hayhurst |
| 5,441,502 A | 8/1995 | Bartlett |
| 5,443,482 A | 8/1995 | Stone et al. |
| 5,454,815 A | 10/1995 | Geisser et al. |
| 5,464,425 A | 11/1995 | Skiba |
| 5,464,427 A | 11/1995 | Curtis et al. |
| 5,466,243 A | 11/1995 | Schmieding et al. |
| 5,480,403 A | 1/1996 | Lee et al. |
| 5,484,451 A | 1/1996 | Akopov et al. |
| 5,486,197 A | 1/1996 | Le et al. |
| 5,520,700 A | 5/1996 | Beyar et al. |
| 5,522,817 A | 6/1996 | Sander et al. |
| 5,522,843 A | 6/1996 | Zang |
| 5,522,844 A | 6/1996 | Johnson |
| 5,527,342 A | 6/1996 | Pietrzak et al. |
| 5,540,718 A | 7/1996 | Bartlett |
| 5,545,180 A | 8/1996 | Le et al. |
| 5,554,171 A | 9/1996 | Gatturna et al. |
| 5,569,306 A | 10/1996 | Thal |
| 5,571,139 A | 11/1996 | Jenkins, Jr. |
| 5,573,543 A | 11/1996 | Akopov et al. |
| 5,573,548 A | 11/1996 | Nazre et al. |
| 5,575,801 A | 11/1996 | Habermeyer et al. |
| 5,578,057 A | 11/1996 | Wenstrom, Jr. |
| 5,584,835 A | 12/1996 | Greenfield |
| 5,584,836 A | 12/1996 | Ballintyn et al. |
| 5,584,860 A | 12/1996 | Goble et al. |
| 5,591,207 A | 1/1997 | Coleman |
| 5,601,557 A | 2/1997 | Hayhurst |
| 5,601,558 A | 2/1997 | Torrie et al. |
| 5,618,314 A | 4/1997 | Harwin et al. |
| 5,626,587 A | 5/1997 | Bishop et al. |
| 5,626,612 A | 5/1997 | Bartlett |
| 5,626,613 A | 5/1997 | Schmieding |
| 5,630,824 A | 5/1997 | Hart |
| 5,643,320 A | 7/1997 | Lower et al. |
| 5,643,321 A | 7/1997 | McDevitt |
| 5,647,874 A | 7/1997 | Hayhurst |
| 5,649,963 A | 7/1997 | McDevitt |
| 5,658,313 A | 8/1997 | Thal |
| 5,662,654 A * | 9/1997 | Thompson ......... A61B 17/0469 606/232 |
| 5,662,662 A | 9/1997 | Bishop et al. |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | Dipoto et al. |
| 5,690,677 A | 11/1997 | Schmieding et al. |
| 5,702,397 A | 12/1997 | Goble et al. |
| 5,713,903 A | 2/1998 | Sander et al. |
| 5,720,753 A | 2/1998 | Sander et al. |
| 5,720,766 A | 2/1998 | Zang et al. |
| 5,725,529 A | 3/1998 | Nicholson et al. |
| 5,725,541 A | 3/1998 | Anspach, III et al. |
| 5,725,557 A | 3/1998 | Gatturna et al. |
| 5,728,100 A | 3/1998 | Skiba |
| 5,728,135 A | 3/1998 | Bregen et al. |
| 5,728,136 A | 3/1998 | Thal |
| 5,733,307 A | 3/1998 | Dinsdale |
| 5,741,282 A | 4/1998 | Anspach, III et al. |
| 5,769,894 A | 6/1998 | Ferragamo |
| 5,782,863 A | 7/1998 | Bartlett |
| 5,782,864 A | 7/1998 | Lizardi |
| 5,782,865 A | 7/1998 | Grotz |
| 5,782,866 A | 7/1998 | Wenstrom, Jr. |

(56) References Cited

U.S. PATENT DOCUMENTS

| | | |
|---|---|---|
| 5,788,063 A | 8/1998 | Van Ness |
| 5,792,142 A | 8/1998 | Galitzer |
| 5,797,963 A | 8/1998 | McDevitt |
| 5,800,447 A | 9/1998 | Wenstrom, Jr. |
| 5,807,403 A | 9/1998 | Beyar et al. |
| 5,810,848 A | 9/1998 | Hayhurst |
| 5,814,051 A | 9/1998 | Wenstrom, Jr. |
| 5,814,070 A | 9/1998 | Borzone et al. |
| 5,814,071 A | 9/1998 | McDevitt et al. |
| 5,817,095 A | 10/1998 | Smith |
| 5,824,011 A | 10/1998 | Stone et al. |
| 5,842,478 A | 12/1998 | Benderev et al. |
| 5,843,087 A | 12/1998 | Jensen et al. |
| 5,851,219 A | 12/1998 | Goble et al. |
| 5,885,294 A | 3/1999 | Pedlick et al. |
| 5,894,921 A | 4/1999 | Le et al. |
| 5,899,920 A | 5/1999 | Desatnick et al. |
| 5,904,704 A | 5/1999 | Goble et al. |
| 5,906,624 A | 5/1999 | Wenstrom, Jr. |
| RE36,289 E | 8/1999 | Le et al. |
| 5,935,129 A | 8/1999 | McDevitt et al. |
| 5,935,134 A | 8/1999 | Pedlick et al. |
| 5,938,686 A | 8/1999 | Benderev et al. |
| 5,941,882 A | 8/1999 | Jammet et al. |
| 5,944,724 A | 8/1999 | Lizardi |
| 5,944,739 A | 8/1999 | Zlock et al. |
| 5,948,000 A | 9/1999 | Larsen et al. |
| 5,948,001 A | 9/1999 | Larsen |
| 5,950,633 A | 9/1999 | Lynch et al. |
| 5,951,559 A | 9/1999 | Burkhart |
| 5,957,924 A | 9/1999 | Toermaelae et al. |
| 5,957,953 A | 9/1999 | Dipoto et al. |
| 5,961,538 A | 10/1999 | Pedlick et al. |
| 5,964,783 A | 10/1999 | Grafton et al. |
| 5,972,000 A | 10/1999 | Beyar et al. |
| 5,980,558 A | 11/1999 | Wiley |
| 5,993,451 A | 11/1999 | Burkhart |
| 5,993,458 A | 11/1999 | Vaitekunas et al. |
| 5,993,477 A | 11/1999 | Vaitekunas et al. |
| 6,007,566 A | 12/1999 | Wenstrom, Jr. |
| 6,019,768 A | 2/2000 | Wenstrom, Jr. et al. |
| 6,027,523 A | 2/2000 | Schmieding |
| 6,029,805 A | 2/2000 | Alpern et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,066,160 A | 5/2000 | Colvin et al. |
| 6,080,154 A | 6/2000 | Reay-Young et al. |
| 6,086,608 A | 7/2000 | Ek et al. |
| 6,093,201 A | 7/2000 | Cooper et al. |
| 6,117,162 A | 9/2000 | Schmieding et al. |
| 6,146,406 A | 11/2000 | Shluzas et al. |
| 6,149,669 A | 11/2000 | Li |
| 6,179,840 B1 | 1/2001 | Bowman |
| 6,183,479 B1 | 2/2001 | Toermälä et al. |
| 6,190,401 B1 | 2/2001 | Green et al. |
| 6,214,031 B1 | 4/2001 | Schmieding et al. |
| 6,241,736 B1 | 6/2001 | Sater et al. |
| 6,264,676 B1 | 7/2001 | Gellman et al. |
| 6,267,718 B1 | 7/2001 | Vitali et al. |
| 6,270,518 B1 | 8/2001 | Pedlick et al. |
| 6,287,324 B1 | 9/2001 | Yarnitsky et al. |
| 6,293,961 B2 | 9/2001 | Schwartz et al. |
| 6,306,159 B1 | 10/2001 | Schwartz et al. |
| 6,319,252 B1 | 11/2001 | McDevitt et al. |
| 6,319,270 B1 | 11/2001 | Grafton et al. |
| 6,319,271 B1 | 11/2001 | Schwartz et al. |
| 6,319,272 B1 | 11/2001 | Brenneman et al. |
| 6,334,446 B1 | 1/2002 | Beyar |
| 6,338,765 B1 | 1/2002 | Statnikov |
| 6,368,350 B1 | 4/2002 | Erickson et al. |
| 6,387,113 B1 | 5/2002 | Hawkins et al. |
| 6,406,480 B1 | 6/2002 | Beyar et al. |
| 6,423,072 B1 | 7/2002 | Zappala |
| 6,461,373 B2 | 10/2002 | Wyman et al. |
| 6,500,169 B1 | 12/2002 | Deng |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,520,980 B1 | 2/2003 | Foerster |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,533,795 B1 | 3/2003 | Tran et al. |
| 6,544,281 B2 | 4/2003 | Elattrache et al. |
| 6,551,330 B1 | 4/2003 | Bain et al. |
| 6,554,852 B1 | 4/2003 | Oberlander |
| 6,569,186 B1 | 5/2003 | Winters et al. |
| 6,569,188 B2 | 5/2003 | Grafton et al. |
| 6,575,984 B2 | 6/2003 | Beyar |
| 6,582,453 B1 | 6/2003 | Tran et al. |
| 6,585,730 B1 | 7/2003 | Foerster |
| 6,616,674 B2 | 9/2003 | Schmieding |
| 6,616,694 B1 | 9/2003 | Hart |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,652,562 B2 | 11/2003 | Collier et al. |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,685,728 B2 | 2/2004 | Sinnott et al. |
| 6,689,153 B1 | 2/2004 | Skiba |
| 6,692,516 B2 | 2/2004 | West et al. |
| 6,716,234 B2 | 4/2004 | Grafton et al. |
| 6,726,707 B2 | 4/2004 | Pedlick et al. |
| 6,743,233 B1 | 6/2004 | Baldwin et al. |
| 6,746,483 B1 | 6/2004 | Bojarski et al. |
| 6,767,037 B2 | 7/2004 | Wenstrom et al. |
| 6,770,073 B2 | 8/2004 | McDevitt et al. |
| 6,770,076 B2 | 8/2004 | Foerster |
| 6,773,436 B2 | 8/2004 | Donnelly et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,887,259 B2 | 5/2005 | Lizardi |
| 6,916,333 B2 | 7/2005 | Schmieding et al. |
| 6,932,834 B2 | 8/2005 | Lizardi et al. |
| 6,942,666 B2 | 9/2005 | Overaker et al. |
| 6,972,027 B2 | 12/2005 | Fallin et al. |
| 6,984,237 B2 | 1/2006 | Hatch et al. |
| 6,986,781 B2 | 1/2006 | Smith |
| 6,989,034 B2 | 1/2006 | Hammer et al. |
| 6,991,636 B2 | 1/2006 | Rose |
| 6,994,719 B2 | 2/2006 | Grafton |
| 7,022,129 B2 | 4/2006 | Overaker et al. |
| 7,029,490 B2 | 4/2006 | Grafton et al. |
| 7,033,380 B2 | 4/2006 | Schwartz et al. |
| 7,037,324 B2 | 5/2006 | Martinek |
| 7,052,499 B2 | 5/2006 | Steger et al. |
| 7,063,717 B2 | 6/2006 | St. Pierre et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,104,999 B2 | 9/2006 | Overaker |
| 7,131,973 B2 | 11/2006 | Hoffman |
| 7,144,414 B2 | 12/2006 | Harvie et al. |
| 7,144,415 B2 | 12/2006 | Del Rio et al. |
| 7,150,757 B2 | 12/2006 | Fallin et al. |
| 7,153,312 B1 | 12/2006 | Torrie et al. |
| 7,163,563 B2 | 1/2007 | Schwartz et al. |
| 7,195,634 B2 | 3/2007 | Schmieding et al. |
| 7,204,839 B2 | 4/2007 | Dreyfuss et al. |
| 7,217,279 B2 | 5/2007 | Reese |
| 7,226,469 B2 | 6/2007 | Benavitz et al. |
| 7,232,455 B2 | 6/2007 | Pedlick et al. |
| 7,235,100 B2 | 6/2007 | Martinek |
| 7,247,164 B1 | 7/2007 | Ritchart et al. |
| 7,250,057 B2 | 7/2007 | Forsberg et al. |
| 7,279,008 B2 | 10/2007 | Brown et al. |
| 7,300,451 B2 | 11/2007 | Crombie et al. |

(56) References Cited

U.S. PATENT DOCUMENTS

| | | | |
|---|---|---|---|
| 7,309,337 B2 | 12/2007 | Colleran et al. | |
| 7,309,346 B2 | 12/2007 | Martinek | |
| 7,320,701 B2 | 1/2008 | Haut et al. | |
| 7,329,272 B2 | 2/2008 | Burkhart et al. | |
| 7,331,982 B1 | 2/2008 | Kaiser et al. | |
| 7,335,221 B2 | 2/2008 | Collier et al. | |
| RE40,237 E | 4/2008 | Bilotti et al. | |
| 7,357,810 B2 | 4/2008 | Koyfman et al. | |
| 7,361,195 B2 | 4/2008 | Schwartz et al. | |
| 7,371,244 B2 | 5/2008 | Chatlynne et al. | |
| 7,381,213 B2 | 6/2008 | Lizardi | |
| 7,390,329 B2 | 6/2008 | Westra et al. | |
| 7,390,332 B2 | 6/2008 | Selvitelli et al. | |
| 7,407,512 B2 | 8/2008 | Bojarski et al. | |
| 7,442,202 B2 | 10/2008 | Dreyfuss | |
| 7,455,674 B2 | 11/2008 | Rose | |
| 7,455,683 B2 | 11/2008 | Geissler et al. | |
| 7,468,074 B2 | 12/2008 | Caborn et al. | |
| 7,485,124 B2 | 2/2009 | Kuhns et al. | |
| 7,517,357 B2 * | 4/2009 | Abrams | A61B 17/0401 606/232 |
| 7,556,638 B2 | 7/2009 | Morgan et al. | |
| 7,556,640 B2 | 7/2009 | Foerster | |
| 7,566,339 B2 | 7/2009 | Fallin et al. | |
| 7,572,275 B2 | 8/2009 | Fallin et al. | |
| 7,572,283 B1 | 8/2009 | Meridew | |
| 7,585,311 B2 | 9/2009 | Green et al. | |
| 7,591,850 B2 | 9/2009 | Cavazzoni et al. | |
| 7,601,165 B2 | 10/2009 | Stone | |
| 7,780,701 B1 | 8/2010 | Meridew et al. | |
| 7,794,484 B2 * | 9/2010 | Stone | A61B 17/0401 606/329 |
| 7,874,839 B2 | 1/2011 | Bouneff | |
| 8,545,535 B2 | 10/2013 | Hirotsuka et al. | |
| 9,463,010 B2 | 10/2016 | Gittings et al. | |
| 9,539,000 B2 | 1/2017 | Hendricksen et al. | |
| 10,383,624 B2 | 8/2019 | Gittings et al. | |
| 2001/0027321 A1 | 10/2001 | Gellman et al. | |
| 2002/0026187 A1 | 2/2002 | Swanson | |
| 2002/0111653 A1 | 8/2002 | Foerster | |
| 2002/0183762 A1 | 12/2002 | Anderson et al. | |
| 2002/0188301 A1 * | 12/2002 | Dallara | A61B 17/068 606/104 |
| 2003/0060835 A1 | 3/2003 | Wenstrom et al. | |
| 2003/0088272 A1 | 5/2003 | Smith | |
| 2003/0105474 A1 | 6/2003 | Bonutti | |
| 2003/0120309 A1 | 6/2003 | Colleran et al. | |
| 2003/0130694 A1 | 7/2003 | Bojarski et al. | |
| 2003/0135151 A1 | 7/2003 | Deng | |
| 2003/0144696 A1 | 7/2003 | Sinnott et al. | |
| 2003/0195563 A1 | 10/2003 | Foerster | |
| 2004/0002734 A1 | 1/2004 | Fallin et al. | |
| 2004/0030341 A1 | 2/2004 | Aeschlimann et al. | |
| 2004/0098045 A1 * | 5/2004 | Grafton | A61B 17/0642 606/213 |
| 2004/0138683 A1 | 7/2004 | Shelton et al. | |
| 2004/0138706 A1 | 7/2004 | Abrams et al. | |
| 2004/0236373 A1 | 11/2004 | Anspach | |
| 2005/0149122 A1 | 7/2005 | McDevitt et al. | |
| 2005/0240199 A1 | 10/2005 | Martinek et al. | |
| 2005/0245932 A1 | 11/2005 | Fanton et al. | |
| 2005/0251208 A1 | 11/2005 | Elmer et al. | |
| 2005/0283192 A1 | 12/2005 | Torrie et al. | |
| 2006/0100630 A1 | 5/2006 | West, Jr. et al. | |
| 2006/0106422 A1 | 5/2006 | Del Rio et al. | |
| 2006/0106423 A1 | 5/2006 | Weisel et al. | |
| 2006/0149286 A1 | 7/2006 | Hoffman et al. | |
| 2006/0178702 A1 * | 8/2006 | Pierce | A61B 17/0401 606/232 |
| 2006/0235413 A1 * | 10/2006 | Denham | A61B 17/0401 606/232 |
| 2006/0276841 A1 | 12/2006 | Barbieri et al. | |
| 2006/0282081 A1 * | 12/2006 | Fanton | A61B 17/0401 606/232 |
| 2006/0282083 A1 | 12/2006 | Fanton et al. | |
| 2006/0293710 A1 | 12/2006 | Foerster et al. | |
| 2007/0005071 A1 | 1/2007 | Kucklick | |
| 2007/0088391 A1 | 4/2007 | McAlexander et al. | |
| 2007/0088412 A1 | 4/2007 | Ashman et al. | |
| 2007/0162022 A1 | 7/2007 | Zhang et al. | |
| 2007/0219557 A1 | 9/2007 | Bourque et al. | |
| 2007/0226719 A1 | 9/2007 | Park et al. | |
| 2007/0255317 A1 | 11/2007 | Fanton et al. | |
| 2007/0260259 A1 | 11/2007 | Fanton et al. | |
| 2008/0009904 A1 | 1/2008 | Bourque et al. | |
| 2008/0021474 A1 | 1/2008 | Bonutti et al. | |
| 2008/0027444 A1 | 1/2008 | Malek | |
| 2008/0051836 A1 | 2/2008 | Foerster et al. | |
| 2008/0054814 A1 | 3/2008 | Deppe et al. | |
| 2008/0058816 A1 | 3/2008 | Philippon et al. | |
| 2008/0086072 A1 | 4/2008 | Bonutti et al. | |
| 2008/0103528 A1 | 5/2008 | Zirps et al. | |
| 2008/0109080 A1 | 5/2008 | Aeschlimann et al. | |
| 2008/0147119 A1 | 6/2008 | Cauldwell et al. | |
| 2008/0188854 A1 | 8/2008 | Moser | |
| 2008/0275469 A1 | 11/2008 | Fanton et al. | |
| 2008/0281325 A1 | 11/2008 | Stone et al. | |
| 2008/0306510 A1 | 12/2008 | Stchur | |
| 2009/0012617 A1 | 1/2009 | White et al. | |
| 2009/0069845 A1 | 3/2009 | Frushell et al. | |
| 2009/0088798 A1 | 4/2009 | Snyder et al. | |
| 2009/0099598 A1 | 4/2009 | McDevitt et al. | |
| 2010/0006902 A1 | 1/2010 | Becker et al. | |
| 2010/0016892 A1 | 1/2010 | Kaiser et al. | |
| 2010/0016902 A1 | 1/2010 | Paulk et al. | |
| 2010/0082072 A1 | 4/2010 | Sybert et al. | |
| 2010/0121355 A1 | 5/2010 | Gittings et al. | |
| 2010/0292731 A1 | 11/2010 | Gittings et al. | |
| 2010/0292732 A1 | 11/2010 | Hirotsuka et al. | |
| 2010/0292733 A1 | 11/2010 | Hendricksen et al. | |
| 2011/0313453 A1 | 12/2011 | Krumme et al. | |
| 2013/0345746 A1 | 12/2013 | Gittings et al. | |
| 2014/0005720 A1 | 1/2014 | Hirotsuka et al. | |
| 2015/0112384 A1 | 4/2015 | Hirotsuka et al. | |
| 2017/0020505 A1 | 1/2017 | Gittings et al. | |
| 2017/0071594 A1 | 3/2017 | Hendricksen et al. | |

FOREIGN PATENT DOCUMENTS

| | | |
|---|---|---|
| GB | 2084468 A | 4/1982 |
| WO | WO-9529637 A1 | 11/1995 |
| WO | WO-9730649 A1 | 8/1997 |
| WO | WO-03096908 A2 | 11/2003 |
| WO | WO-03096908 A3 | 5/2004 |
| WO | WO-2006037131 A2 | 4/2006 |
| WO | WO-2006039296 A2 | 4/2006 |
| WO | WO-2007078281 A2 | 7/2007 |
| WO | WO-2008054814 A2 | 5/2008 |
| WO | WO-2008054814 A3 | 6/2008 |
| WO | WO-2008109087 A1 | 9/2008 |
| WO | WO-2008124206 A2 | 10/2008 |
| WO | WO-2008124463 A2 | 10/2008 |
| WO | WO-2008124206 A3 | 12/2008 |
| WO | WO-2009023034 A1 | 2/2009 |
| WO | WO-2009039513 A1 | 3/2009 |
| WO | WO-2010132307 A1 | 11/2010 |
| WO | WO-2010132309 A1 | 11/2010 |
| WO | WO-2010132310 A1 | 11/2010 |

OTHER PUBLICATIONS

Ambrose et al., "Bioabsorbable Implants: Review of Clinical Experience in Orthopedic Surgery," Annals of Biomedical Engineering, Jan. 2004; 32(1):171-177.

Arthrex. Acetabular Labral Repair [brochure], Arthrex, Inc., 2007, 6 pages total; retrieved from the Internet:<http://arthromed.org/pdf/hip/Surgical%20Techniques/Acetabular%20Labral%20Repair%20using%20the%20PushLock%20Knotless%20Anchor%20System.pdf>.

Arthrex. Bio-Corkscrew Anchor FT and Corkscrew FT II Suture Anchors [brochure], Arthrex, Inc., 2005, 6 pages total; retrieved

(56) References Cited

OTHER PUBLICATIONS from the Internet:<http://www.rcsed.ac.uk/fellows/lvanrensburg/classification/surgtech/arthrex/arthrex%20manuals/biocorkscrew.pdf>.
Arthrex. Bio-SutureTak Bankart & SLAP Repair [brochure], Arthrex, Inc., 2007, 6 pages total; retrieved from the Internet:<http://depts.washington.edu/shoulder/Surgery/ArthroscopicTechniques/Arthrex/Bio-SutureTak-SLAP-Bankart-Repair.pdf>.
Arthrex, Inc., 2.5 mm PushLock® Knotless Suture Anchor [brochure], 2007, 2 pages total.
Arthrex, Inc., "4.5 mm/6.7 mm Low Profile Screw System Surgical Technique" [brochure], 2009, 6 pages total.
Arthrex, Inc., "Acetabular Labral Repair Using the Bio-SutureTak® Suture Anchor System Surgical Technique" [brochure], 2007, 6 pages total.
Arthrex, Inc., "Achilles SutureBridgeTM Surgical Technique" [brochure], 2009, 6 pages total.
Arthrex, Inc., "ACL Graft Tensioning using the Suture Tensioner with Tensionmeter Surgical Technique" [brochure], 2009, 6 pages total.
Arthrex, Inc., "AdapteurTM Power System II" [brochure], 2008, 12 pages total.
Arthrex, Inc., "Advanced Technology" [brochure], 2008, 15 pages total.
Arthrex, Inc., "All-Inside BTB ACL RetroConstructionTM with Bone-Tendon-Bone Grafts Surgical Technique" [brochure], 2007, 8 pages total.
Arthrex, Inc., "Arthrex 300 Power System—Small Bone" [brochure], undated, 2 pages total.
Arthrex, Inc., "Arthrex 600 Power System—Small Bone" [brochure], undated, 2 pages total.
Arthrex, Inc., "Arthrex ACPTM Double Syringe System" [brochure], 2009, 6 pages total.
Arthrex, Inc., "Arthrex Bio-Composite Suture Anchors", p. 9 of 510(k) Summary, FDA Approval Letter and Indications of Use for 510(k) No. K082810, Jan. 2009, 6 pages total.
Arthrex, Inc., "Arthrex Flatfoot Solutions"[brochure], 2008, 2 pages total.
Arthrex, Inc., "Arthrex Hallux Valgus Solutions"[brochure], 2008, 2 pages total.
Arthrex, Inc., "Arthrex PushLock, Tak, and Corkscrew Products", p. 12 of 510(k) Summary, FDA Approval Letter and Indications of Use for 510(k) No. K061863, Oct. 2006, 6 pages total.
Arthrex, Inc., "Arthroscopic Meniscal Repair: Arthroscopic All-Inside Meniscal Repair with the Mensical ViperTM and DarkstickTM Surgical Technique" [brochure], 2006, 6 pages total.
Arthrex, Inc., "Arthroscopic Rotator Cuff Repair: Bio-Corkscrew® Suture Anchor Rotator Cuff Repair Surgical Technique" [brochure], 2007, 6 pages total.
Arthrex, Inc., "Arthroscopy Instruments" [brochure], 2008, 12 pages total.
Arthrex, Inc., "Beach Chair Lateral Traction Device Assembly Instructions" [instructions for use], 2006, 2 pages total.
Arthrex, Inc., "BioComposite SutureTak, BioComposite Corkscrew FT and BioComposite PushLock: An In Vitro Degradation Study" [white paper], Arthrex Research and Development, 2009, 1 page.
Arthrex, Inc., "BioCompositeTM Interference Screws: A Stronger Turn in ACL/PCL Reconstruction," 2008, 56 pages total.
Arthrex, Inc., "BioCompositeTM Interference Screws for ACL and PCL Reconstruction," Arthrex Research and Development, 2008, 5 pages total.
Arthrex, Inc., "Bio-Compression Screw System" [brochure], 2008, 6 pages total.
Arthrex, Inc., "Bio-FASTak® Bankart Repair Surgical Technique" [brochure], 2007, 6 pages total.
Arthrex, Inc., "Biomechanical Testing Comparison of Cayenne Medical and Arthrex, Inc. Repair Products" [white paper], Arthrex Research and Development, 2009, 1 page total.
Arthrex, Inc., "Bio-PostTM and Washer System" [brochure], 2001, 2 pages total.
Arthrex, Inc., "Bio-SutureTak Suture Anchor" [brochure], 2006, 2 pages total.
Arthrex, Inc., "Bio-TenodesisTM Screw System" [brochure], 2008, 6 pages total.
Arthrex, Inc., "Bone, Tendon or Ligament Repair?" [brochure], 2004, 1 page total.
Arthrex, Inc., "ClearCut Burrs" [brochure], 2006, 2 pages total.
Arthrex, Inc., "Comprehensive Solutions for Forefoot and Midfoot Surgery using the Mini TightRope® System—Five Surgical Techniques" [brochure], 2008, 13 pages total.
Arthrex, Inc., "CoolCut Series: Shaver Blades and Burrs" [brochure], 2009, 4 pages total.
Arthrex, Inc., "Scorpion—Fulfilling the Need for Precision and Speed in Arthroscopic Rotator Cuff Repair" [brochure], 2008, 6 pages total.
Arthrex, Inc., "Double Row Rotator Cuff Repair using the Bio-Corkscrew® FT Surgical Technique" [brochure], 2007, 6 pages total.
Arthrex, Inc., "Elbow/Ankle Arthroscopy Instrument Set" [brochure], 2007, 8 pages total.
Arthrex, Inc., "Endoscopic Carpal Tunnel Release System" [brochure], 2000, 2 pages total.
Arthrex, Inc., "FiberWire® Braided Composite Suture" [brochure], 2008, 8 pages total.
Arthrex, Inc., "FiberWire® Collective Summary of Strength and Biocompatibility Testing Data Comparisons of Polyester and Polyblend Sutures" [white paper], 2006, 4 pages total.
Arthrex, Inc., "FiberWire® Confidence After Closure" [brochure], 2008, 6 pages total.
Arthrex, Inc., "FiberWire® Orthopaedic Composite Suture" [sell sheet], 2007, 2 pages total.
Arthrex, Inc., "FlipCutter ACL Reconstruction TM: ACL Reconstruction using the FlipCutterTM and the Constant Femoral Guide Surgical Technique" [brochure], 2008, 6 pages total.
Arthrex, Inc., "FlipCutterTM" [brochure], 2009, 2 pages total.
Arthrex, Inc., "Freedom in Anatomic Femoral Socket Placement" [brochure], 2009, 2 pages total.
Arthrex, Inc., "Fulfilling the Need for Precision and Speed Rotator Cuff Repair" [brochure], 2009, 12 pages total.
Arthrex, Inc., "Shaver Blades and Burrs" [brochure], 2005, 1 page total.
Arthrex, Inc., In Arthroscopic Surgery, You Can't Treat It If You Can't Reach It[brochure], 2007, 12 pages total.
Arthrex, Inc., "Single Use Disposable Shaver Blades and Burrs" [brochure], 2008, 2 pages total.
Arthrex, Inc., "Innovative Solutions for Hip Arthroscopy" [brochure], 2008, 16 pages total.
Arthrex, Inc., "Knotless Rotator Cuff Repair: SpeedBridgeTM and SpeedFixTM Knotless Rotator Cuff Repair using the SwiveLockTM C and FiberTape® Surgical Technique" [brochure], 2008, 8 pages total.
Arthrex, Inc., "Knotless SingleRow Rotator Cuff Repair using the PushLockTM and FiberTape® Surgical Technique" [brochure], 2007, 4 pages total.
Arthrex, Inc., "Small Joint: Fracture—Fusion—Osteotomy Fixation Options" [brochure], 2007, 2 pages total.
Arthrex, Inc., "MultiFire Scorpion TM Independently Pass Two FiberWire® Suture Tails Through Tissue Without Scorpion Removal" [brochure], 2009, 4 pages total.
Arthrex, Inc., New Materials in Sports Medicine [white paper], 2006, 7 pages total.
Arthrex, Inc., "Next Generation In Knee Ligament Reconstruction & Repair Technology" [brochure], 2009, 42 pages total.
Arthrex, Inc., "Orthopaedic Procedure Electrosurgical System (ORES®)" [brochure], 2008, 11 pages total.
Arthrex, Inc., "OSferion: Porous Trapezoid 6-TCP Synthetic Grafting of BTB Autograft Harvest Sites" [brochure], 2008, 18 pages total.
Arthrex, Inc., "OSferion: Porous Trapezoid 6-TCP Synthetic Wedge Grafting of Tibial and Femoral Opening Wedge Osteotomy Sites" [brochure], 2009, 6 pages total.
Arthrex, Inc., "Percutaneous Glenohumeral Repair with SutureTak® Implants" [brochure], 2009, 2 pages total.

(56) References Cited

OTHER PUBLICATIONS

Arthrex, Inc., "ProStop® and ProStop® Plus For Correction of Posterior Tibial Tendon Dysfunction," [brochure], 2009, 6 pages total.
Arthrex, Inc., "ProWickTM Knee Postoperative and Cold Therapy Dressing System" [brochure], 2009, 4 pages total.
Arthrex, Inc., "ProWickTM Shoulder Postoperative and Cold Therapy Dressing System" [brochure], 2009, 4 pages total.
Arthrex, Inc., "Pull Out Strength of a 3.5 mm Bio-PushLock (AR-1926B)" [white paper], Arthrex Research and Development Nov. 10, 2005, 1 page total.
Arthrex, Inc., "PushLock®" [advertisement], 2008, 1 page total.
Arthrex, Inc., "PushLock® Bankart & SLAP Repair: PushLock® Knotless Anchor for Bankart & SLAP Repair Surgical Technique" [brochure], 2009, 8 pages total.
Arthrex, Inc., "PushLock® Knotless Instability Repair" [brochure], 2009, 12 pages total.
Arthrex, Inc., PushLockTM [directions for use], DFU-0099, Revision 8, 2 page total.
Arthrex, Inc., "Raising the Bar in Arthroscopic Imaging and Resection Technology" [brochure], 2009, 8 pages total.
Arthrex, Inc., "RetroConstruction TM Minimally Invasive Options for Anatomic ACL/PCL Reconstruction" [brochure], 2009, 11 pages total.
Arthrex, Inc., The Arthrex Chondral DartTM [brochure], 2006, 4 pages total.
Arthrex, Inc., The Continuous Wave III Arthroscopy Pump: Clear Vision in Arthroscopic Fluid Management [brochure], 2006, 12 pages total.
Arthrex, Inc., The Fully Threaded Family of Soft Tissue Repair Anchors: Cortical Cancellous Fixation with Fiberwire® Composite Suture for Superior Repair Strength [brochure], 2008, 6 pages total.
Arthrex, Inc., The Next Generation in Foot and Ankle Repair Technology [brochure], 2009, 44 pages total.
Arthrex, Inc., The Next Generation in Hand, Wrist and Elbow Repair Technology [brochure], 2009, 28 pages total.
Arthrex, Inc., The Next Generation in Shoulder Repair Technology [brochure], 2008, 24 pages total.
Arthrex, Inc., The Next Generation in Shoulder Repair Technology [brochure], 2009, 26 pages total.
Arthrex, Inc., The OATS® Sterile, Single Use Kit [brochure], 2007, 2 pages total.
Arthrex, Inc., "Thumb UCL Repair/Reconstruction: 2.5 mm PushLock®/3 mm×8 mm BioTenodesisTM Thumb Collateral Ligament Repair/Reconstruction" [brochure], 2008, 8 pagest total.
Arthrex, Inc., "Transtibial ACL Reconstruction with Soft Tissue Grafts Surgical Technique" [brochure], 2007, 5 pages total.
Arthrex, Inc., "Trim-It Drill Pin® Osteotomy Fixation Kit" [brochure], 2009, 6 pages total.
Arthrex, Inc., "Trim-It Drill Pin TM The Need to Remove Hardware is Disappearing" [brochure], 2009, 2 pages total.
Arthrex, Inc., "Trim-ItTm Screw System" [brochure], 2006, 6 pages total.
Arthrex, Inc., "SutureLasso TM SD Products Reference Guide" [brochure], 2007, 1 page total.
Arthrex, Inc., "SutureTakTm Suture Anchors" [directions for use], DFU-0069, Revision 10, 2 page total.
Arthrex, Inc., "V-TakTm Soft Tissue Anchor" [brochure], 2006, 6 pages total.
Arthrex, Inc., "Wishbone TM Series Arthroscopy Instruments" [brochure], 2008, 8 pages total.
Arthrex, Inc., "SwiveLockTM & FiberChain TM Knotless Rotator Cuff Repair Surgical Technique" [brochure], 2007, 8 pages total.
ArthroCare Corporation, "LabraLock P Knotless Implant w/Inserter Handle" [website], 1 page; retrieved:< http://www.arthrocaresportsmedicine.com/products/view/430>.
ArthroCare Corporation, "Magnum® MP Suture Implant" [brochure], 2009, 2 pages total.
ArthroCare Corporation, "Mini Magnum® Knotless Fixation Implant" [brochure], 2009, 2 pages total.
ArthroCare Corporation, "Mini Magnum Knotless Implant w/Inserter Handle" [website], 1 page; retrieved:< http://www.arthrocaresportsmedicine.com/products/view/429>.
ArthroCare Corporation, "SpeedScrewTM Fully Threaded OPUS® Knotless Fixation Implant" [brochure], 2009, 2 pages total.
ArthroCare Corporation, The OPUS® AutoCuff System Featuring SpeedScrew for Rotator Cuff Repair Technical Guide [brochure], 2009, 8 pages total.
ArthroCare Corporation, The OPUS® AutoCuff System for Rotator Cuff Repair Technical Guide [brochure], 2008, 8 pages total.
ArthroCare. OPUS LabraFix Knotless System [brochure], ArthroCare Corporation, 2008, A1027 Rev D, 6 pages total; retrieved:<http://www.arthrocaresportsmedicine.com/files/datasheets/A1027D.pdf>.
ARTHROTEK®. Charlotte TM Shoulder System: Arthroscopic Bankart Lesion Repair Using the 3.5 mm LactoScrew Suture Anchor [brochure], a Biomet Company. 2006, 4 pages total.
ARTHROTEK®. Charlotte TM Shoulder System [brochure], a Biomet Company. 2006, 16 pages total.
ARTHROTEK®. CharlotteTM Shoulder System: SLAP Lesion Repair Using the 3.5 mm LactoScrew Suture Anchor [brochure], a Biomet Company. 2002, 4 pages total.
ARTHROTEK®. MaxBraidTM PE Suture [brochure], a Biomet Company. 2004, 2 pages total.
ARTHROTEK®. MicroMax-fly Resorbable Suture Anchor [brochure], a Biomet Company. 2006, 8 pages total.
Barber et al., "Suture Anchors—Update 1999," Arthroscopy, Oct. 1999; 15(7):719-725.
Bardana et al., The Effect of Suture Anchor Design and Orientation on Suture Abrasion: An In Vitro Study, Arthroscopy, Mar. 2003; 19(3,):274-281.
Benthien et al., "Cyclic Loading Achilles Tendon Repairs: A Comparison of Polyester and Polyblend Suture," Foot Ankle Int. Jul. 2006;27(7):512-518.
Biomet, Inc., MicroMax-rm Resorbable Suture Anchor [website], 1 page; retrieved from the Internet: http://www.biomet.com/sportsMedicine/productDetail.cfm?category=23&subCategory=33&product=108.
Biomet Sports Medicine, Hitch Suture Anchor [brochure], 2008, 2 pages total.
Biomet Sports Medicine, MicroMax TM Flex Suture Anchor MicroMaxTM Resorbable Suture Anchor [brochure], 2009, 20 pages total.
Biomet Sports Medicine, MicroMaxTm Flex Suture Anchor [advertisement], 2009, 2 pages total.
Biomet Sports Medicine, The Material Difference: Options for Rotator Cuff Repair, Labral Repairand Suture Management [brochure], 2008, 12 pages total.
Blokhuis et al., "Properties of Calcium Phosphate Ceramics in Relation to Their In Vivo Behavior," J Trauma. Jan. 2000;48(1):179-86.
Brady et al., "Arthroscopic Rotator Cuff Repair: Establishing the Footprint," Techniques in Shoulder & Elbow Surgery, Dec. 2005; 6(4):242-251.
Burkhart, "Arthroscopic Repair of Retracted Adhesed Rotator Cuff Tears and Subscapularis Tears: The Effective Use of Interval Slide Releases," Int J Shoulder Surg 2007; 1(1):39-44; retrieved from the internets http://www.internationalshoulderjournal.Org/text.asp?2007/1/1/39/30677>.
Burkhart, "Arthroscopic Rotator Cuff Repair: Indications and Technique," Operative Techniques in Sports Medicine, Oct. 1997; 5(4):204-214.
Burkhart et al., "SLAP Lesions in the Overhead Athlete," Operative Techniques in Sports Medicine, Jul. 2000; 8(3):213-220.
Burkhart et al., "Loop Security as a Determinant of Tissue Fixation Security," Arthroscopy, Oct. 1998;14(7):773-776.
Burkhart, "Knotless Self-Reinforcing Rotator Coff Repair with FiberChain-SwiveLock System" [video recording], ArthroCologne, 2nd International Symposium on Operative and Biologic Treatments in Sports Medicine, Cologne, Germany, Jun. 15-16, 2007; retrieved from the Internet: http://www.arthrocologne.com/SwiveLock-Rotator-Cuff-Repair.16361.html.

(56) References Cited

OTHER PUBLICATIONS

Burkhart, New Thoughts on SLAP Lesions, Arthroscopy and Arthroplasty of the Shoulder 15th Annual San Diego, 1998; pp. 351-355.
Bynum et al., "Failure Mode of Suture Anchors as a Function of Insertion Depth," Am J Sports Med Jul. 2005; 33(7):1030-1034.
C2M Medical, Inc., "CinchTM Knotless Fixation Implant System", pp. 63-65 of 510(k) Summary, FDA Approval Letter and Indications of Use for 510(k) No. K073226, Dec. 2007, 5 pages total.
Caborn et al., "A Biomechanical Comparison of Initial Soft Tissue Tibial Fixation Devices: The Intrafix Versus a Tapered 35-mm Bioabsorbable Interference Screw," Am J Sports Med, Jun. 2004; 32(4):956-961.
Chang et al., "Biomechanical Evaluation of Meniscal Repair Systems: A Comparison of the Meniscal Viper Repair System, the Vertical Mattress FasT-Fix Device, and Vertical Mattress Ethibond Sutures," Am J Sports Med, Dec. 2005; 33(12):1846-1852.
Chokshi et al., The effect of arthroscopic suture passing instruments on rotator cuff damage and repair strength, Bulletin of the NYU Hospital for Joint Diseases, Winter-Spring, 2006; 63(3/4): 123-125; retrieved from the Internet:<http://www.nyuhjdbulletin.org/Mod/BulletinA/63N3-4/DocsA/63N3-4_11.pdf>.
CONMED Corporation, "Bio Mini-Revo® Anchor" [website], 1 page; retrieved from the Internet:< http://www.conmed.com/products_shoulder_biominirevo.php>.
CONMED Corporation "Bio Mini-Revo Suture Anchor", 510(k) Summary, FDA Approval Letter, FDA Approval Letter, and Indications of Use for 510(k) No. K073226, Jul. 2008, 5 pages total.
CONMED Linvatec, "Arthroscopy Product Catalog" [catalog], 2009, 194 pages total.
CONMED Linvatec, "Bio Mini-Revo TM Surgical Technique" [brochure] 2006, 12 pages total.
CONMED Linvatec, "Bio-Anchor® Shoulder Instability Repair System" [website], 2006, 1 page; retrieved from the Internet:< http://www.conmed.com/products_shoulder_bioanch.php>.
CONMED Linvatec, "Course: Bio Mini-Revo TM Surgical Technique—Designed in conjunction with Stephen J. Snyder, MD" [Slideshow] 2006, 26 pages; retrieved from the Internet:< http://www.conmed.com/SurgicalTechniques/BioMiniRevo.swf>.
CONMED Linvatec, "DuetTM Suture Anchor" [brochure], 2008, 4 pages total.
CONMED Linvatec, "Shoulder Restoration System" [brochure], 2009, 4 pages total.
CONMED Linvatec, "Shoulder Restoration System: PopLokTM Deployment Stages" [brochure], 2009, 2 pages total.
CONMED Linvatec, "Shoulder Restoration System" [website], 2009, 1 page; retrieved from the Internet:< http://srs.linvatec.com/>.
CONMED Linvatec, "Linvatec SRS Shoulder Restoration System: Simple Solutions for Complex Procedures" [website], 2009, 2 pages; retrieved from the Internet:<http://www.conmed.com/products_shoulder_srs_system.php?SelectCountry=0THER+COUNTRY.>.
CONMED Linvatec, "Paladin TIVI Rotator Cuff Anchor" [brochure], 2009, 2 pages total.
CONMED Linvatec, "Spectrum® II Soft Tissue Repair System" [brochure], 2006, 4 pages total.
CONMED Linvatec, "Spectrum® MVPTM" [brochure], 2008, 4 pages total.
CONMED Linvatec, "Super Shuttle TM" [brochure], 2009, 2 pages total.
Covidien AG, "HerculonTM Soft Tissue Fixation System—Bringing greater pull-out strength to rotator cuff repair" [brochure], 2008, 4 pages total.
Daculsi et al., "Current State of the Art of Biphasic Calcium Phosphate Bioceramics," Journal of Materials Science, Mar. 2003; 14(3):195-200.
Depuy Mitek, Inc, a Johnson & Johnson Company, "Biocryl Rapide—TCP/PLGA Composite" [brochure], 2007, 4 pages total.
Depuy Mitek, Inc, a Johnson & Johnson Company, "BioKnotlessTM RC Suture Anchor: Rotator Cuff Repair Surgical Technique" [brochure], 2006, 6 pages total.
Depuy Mitek, Inc, a Johnson & Johnson Company, "ExpresSewTM: A Single-Step Passer Under 5 mm" [brochure], 2005, 2 pages total.
Depuy Mitek, Inc, a Johnson & Johnson Company, "ExpresSewTM Flexible Suture Passer" [instructions for use], Aug. 2007, 124 pages total.
Depuy Mitek, Inc, a Johnson & Johnson Company, "ExpresSewTM II Flexible Suture Passer" [instructions for use], Oct. 2006, 105 pages total.
Depuy Mitek, Inc, a Johnson & Johnson Company, "ExpresSewTM II: Surgical Technique" [brochure], 2007, 8 pages total.
Depuy Mitek, Inc, a Johnson & Johnson Company, "ExpresSewTM Surgical Technique" [brochure], 2005, 2 pages total.
Depuy Mitek, Inc, a Johnson & Johnson Company, "Healix BRTM" [brochure], 2009, 2 pages total.
Depuy Mitek, Inc, a Johnson & Johnson Company, "Healix PEEKTM—Dual Threaded Suture Anchor" [brochure], 2009, 2 pages total.
Depuy Mitek, Inc, a Johnson & Johnson Company, "Lupine T'" BR & BioknotlessTM BR Anchors . . . Now with Biocryl Rapide—Biocryl Rapide has refined our Suture Anchors as "Bio-Replaceable" [brochure], 2007, 4 pages total.
Depuy Mitek, Inc, a Johnson & Johnson Company, "Mitek Suture Grasper" [instructions for use], 2007, 60 pages total.
Depuy Mitek, Inc, a Johnson & Johnson Company, "Palenlok® RC—Quick Anchor Plus® Absorbable" [brochure] 2006, 2 pages total.
Depuy Mitek, Inc, a Johnson & Johnson Company, PathSeekerTM Flexible Suture Grasper [brochure], 2005, 2 pages total.
Depuy Mitek, Inc, a Johnson & Johnson Company, "PathSeekerTM Suture Passer" [instructions for use], 2007, 174 pages total.
Depuy Mitek, Inc, a Johnson & Johnson Company, SpiraLokTM Absorbably Dual-Eyelet Theaded Suture Anchor [brochure], 2005, 2 pages total.
Depuy Mitek, Inc, a Johnson & Johnson Company, "Quick Anchor® Plus Family" [brochure], 2005, 2 pages total.
Depuy Mitek, Inc, a Johnson & Johnson Company, VersalokTM Anchor [instructions for use], Aug. 2007, 92 pages total.
Depuy Mitek, Inc, a Johnson & Johnson Company, Procedural Solutions in Shoulder Repair [advertorial and detail],2005; retrieved from the Internet: http://issuu.com/valmaass/docs/mitek_advertorial?mode=a_p.
Dines et al., "Horizontal Mattress With a Knotless Anchor to Better Recreate the Normal Superior Labrum Anatomy," Arthroscopy, Dec. 2008;24(12):1422-1425.
Esch, "Arthroscopic Rotator Cuff Repair with the Elite TM Shoulder System," A Smith & Nephew Techique Plus T' Illustrated Guide, 2001, 16 pages total.
Ethicon, Inc., a Johnson & Johnson Company, Mitek® Products, "Absorbable Soft Anchor PANALOK®" [brochure] 2001, 2 pages; can be retrieved from the Internet:<www.shoulderdoc.co.uk/documents/mitek_panalok.pdf>.
Ethicon, Inc., a Johnson & Johnson Company, Mitek® Products BioknotlessTM Anchors: The First Absorbable Knotless Suture Anchor [brochure], 2007, 2 pages total.
"European search report and search opinion dated Apr. 2, 2015 for EP Application 10775303.0."
European search report and search opinion dated Apr. 15, 2016 for EP Application No. 10775301.4.
"European search report and search opinion dated Apr. 20, 2015 for EP Application No. 10775304.8."
"Final Office action dated Jun. 26, 2018 for U.S. Appl. No. 14/585,654".
Fox et al., "Update on Articular Cartilage Restoration," Techniques in Knee Surgery, Mar. 2003; 2(1):2-17.
Gartsman, "Arthroscopic Repair of Full-Thickness Tears of the Rotator Cuff," The Journal of Bone and Joint Surgery, 1998; 80:832-840.
Gartsman et al., "Arthroscopic Rotator Cuff Repair," Techniques in Shoulder and Elbow Surgery, 1999, pp. 1-7.
Gartsman, Shoulder Series Technique Guide: Bankart Repair Using the Smith & Nephew Bioraptor 2.9 Suture Anchor [brochure], Smith & Nephew, Inc., Sep. 2004, Rev. A, 7 pages total; retrieved from the Internet: http://global.smith-nephew.com/cps/rde/xbcr/smithnephewls/V1-1061563A_bioraptorpdf.

(56) References Cited

OTHER PUBLICATIONS

Gill, The Treatment of Articular Cartilage Defects Using Microfracture and Debridement, Am J Knee Surg 2000;13(1):33-40.
Green et al., "Arthroscopic versus open Bankart procedures: a comparison of early morbidity and complications," Arthroscopy, 1993; 9(4):371-374.
Guanche et al., "Labral Repair" [video recording], A young track athlete with a pincer lesion in her hip undergoes an arthroscopic labral takedown and repair by Carlos Guanche, MD at Southern California Orthopedic institute in Van Nuys, CA. Dr. Guanche performs complex hip arthroscopic procedures including resection of cam lesions, labral repairs, psoas releases and abductor repairs, posted on the Internet:<http://www.youtube.com/watch?v=onCIESDRVZM&feature=channel_page> on Jun. 18, 2008.
Guanche, "Large Hip Labral Repair Using PushLockTM Anchor" [video recording], Arthroscopic surgery of a hip labral repair with a knotless anchor performed by Dr. Carlos Guanche in Van Nuys, CA, posted on the Internet:<http://www.youtube.com/watch?v=t04fj2TcXv0>on Mar. 25, 2008.
Halbrecht, "Versalok: A New technique for Arthroscopic Knotless Rotator Cuff Repair" [presentation], Mitek Sponsored Dinner Meeting. Tuscon AZ. Jun. 5, 2007; retrieved from the Internet:< http://www.iasm.com/pdfs/KnotlessArthroscopicRotatorCuffRepairUsingVersalok.pdf>, 44 pages total.
Hughes, The Kinematics and Kinetics of Slipknots for Arthroscopic Bankart Repair, Am J Sports Med, Nov. 2001; 29( 6):738-745.
International search report and written opinion dated Jul. 2, 2010 for PCT/US2010/034104.
International search report and written opinion dated Jul. 2, 2010 for PCT/US2010/034118.
International search report and written opinion dated Jul. 9, 2010 for PCT/US2010/034115.
Jeys et al., "Bone Anchors or Interference Screws? A Biomechanical Evaluation for Autograft Ankle Stabilization," Am J Sports Med, Oct. 2004; 32( 7):1651-1659.
KFX® Medical, Arthroscopic Double Row Rotator Cuff Repair [procedural Video], Performed by Joe Tauro, M.D., Toms River, NJ; can be view at:< http://www. kfxmed ical. com/technology_proced u re. htm>.
KFX® Medical, "Arthroscopic PASTA lesion repair using the SutureCross® System" [procedural Video] Performed by Joe Tauro, M.D., Toms River, NJ; can be view at: http://www.kfxmedical.com/technology_procedure_pasta_video.htm.
KFX® Medical, The PASTAFxTM System: No. need to Tear to Repair [website]; retrieved from the internet:<http://www.kfxmedical.com/product_pastafx.htm>, 2 pages total.
KFX® Medical, The PASTAFxTM System: Simplified PASTA Repair [datasheet] 2008, 2 pages total.
KFX® Medical, The PASTAFxTM System Surgical Technique: Simplified PASTA Rotator Cuff Repair [technique guide], 2008, 8 pages total.
KFX® Medical, "SutureCross® Knotless Anatomic Fixation System: Double Row Fixation for Rotator Cuff Repair Animation" [video screenshots] 2008, 52 pages total.; video available online at<http://www.kfxmedical.com/video/SURGTECH9-23.wmv>.
KFX® Medical, "SutureCross® Knotless Anatomic Fixation System: Double Row Fixation Rotator Cuff Repair Surgical Technique" [brochure], 2008, 12 pages total.
KFX® Medical, "SutureCross® Knotless Anatomic Fixation System: Double Row Rotator Cuff Fixation" [website]; retrieved from the Internet:<http://www.kfxmedical.com/product_suturecross.htm>, 1 page.
KFX® Medical, "SutureCross® Knotless Anatomic Fixation System: Rotator Cuff Repair" [datasheet], 2008, 2 pages total.
Khabie et al., "Fixation Strength of Suture Anchors After Intraoperative Failure of the First Anchor," 45th Annual Meeting of Orthopaedic Research Society, Feb. 1-4, 1999, Anaheim, p. 1074 ; retrieved from the Internet:< http://www.ors.org/web/Transactions/45/1074.PDF>.
Langdown et al., In Vivo Evaluation of 6-TCP Bone Graft Substitutes in a Bilateral Tabial Defect Model, Paper No. 1712, 52nd Annual Meeting of the Orthopaedic Research Society, The Lakeside Center, McCormick Place, Chicago, IL, Mar. 19-22, 2006, 1 page total.
Larson et al., "Arthroscopic Management of Femoroacetabular Impingement: Early Outcomes Measures," Arthroscopy. May 2008;24(5):540-546.
Linvatec, a CONMED® Company, "Bio-Anchor® Surgical Technique: Shoulder Instability System" [brochure], 2004, 2 pages; retrieved from the Internet: http://www. con med.com/PDF%20files/CST%203021%20Rev%201%20BioAnchorST.pdf.
Linvatec, a CONMED® Company, "ImpactTM Suture Anchor Surgical Technique" [brochure], 2004, 4 pages total.
Linvatec, "Course: Bio-Anchor® Surgical Technique" [Slideshow], 2004, 13 pages; retrieved from the Internet:< http://www.conmed.com/SurgicalTechniques/BioAnchor.swf>.
Lo et al., "Abrasion Resistance of Two Types of Nonabsorbable Braided Suture," Arthroscopy, Apr. 2008; 20(4):407-413.
Lo et al., "Arthroscopic Knots: Determining the Optimal Balance of Loop Security and Knot Security," Arthroscopy. May 2004;20(5):489-502.
Louden et al., "Tendon Transfer Fixation in the Foot and Ankle: A Biomechnanical Study Evaluating Two Sizes of Pilot Holes for Bioabsorbable Screws," Foot & Ankle International, Jan. 2003; 24(1):67-72.
Ma et al., "Biomechanical Evaluation of Arthroscopic Rotator Cuff Stitches," The Journal of Bone and Joint Surgery, 2004; 86:1211-1216.
McGuire et al., "Bioabsorbable Interference Screws for Graft Fixation in Anterior Cruciate Ligament Reconstruction," Arthroscopy, Jul. 1999; 15(5):463-473.
Menche et al., "Inflammatory Foreign-Body Reaction to an Arthroscopic Bioabsorbable Meniscal Arrow Repair," Arthroscopy. Oct. 1999;15(7):770-772.
Meyer et al., "Mechanical Testing of Absorbable Suture Anchors," Arthroscopy, Feb. 2003; 19(2):188-193.
Middleton et al., "Synthetic Biodegradable Polymers as Orthopedic Devices," Biomaterials, Dec. 2000, 21(23):2335-2346.
Millett et al., "Mattress Double Anchor Footprint Repair: A Novel, Arthroscopic Rotator Cuff Repair Technique," Arthroscopy Oct. 2004; 20(8):875-879.
Morgan, "Arthroscopic Management of Rotator Cuff Tears" [Presentation Outline], The Morgan Kalman Clinic, Wilmington, Delaware, undated, 2 pages.
Murray, Jr., "Arthroscopic Rotator Cuff Repair with a Bioabsorbable Suture Anchor: Preliminary Results," [Abstract] Orthopaedic Associates of Portland, Portland, ME, 1 page.
Notice of allowance dated Mar. 31, 2016 for U.S. Appl. No. 13/749,038.
Notice of allowance dated Aug. 2, 2013 for U.S. Appl. No. 12/776,208.
Notice of allowance dated Aug. 26, 2016 for U.S. Appl. No. 13/855,445.
Office Action dated Jan. 5, 2018 from U.S. Appl. No. 14/804,178.
Office Action dated Mar. 23, 2017 for U.S. Appl. No. 14/585,654.
Office action dated Apr. 20, 2015 for U.S. Appl. No. 13/692,596.
Office action dated May 31, 2019 for U.S. Appl. No. 15/190,332.
Office action dated Jun. 5, 2012 for U.S. Appl. No. 12/605,065.
Office action dated Jun. 18, 2013 for U.S. Appl. No. 12/776,208.
"Office action dated Aug. 7, 2018 for U.S. Appl. No. 14/804,178".
"Office action dated Sep. 11, 2015 for U.S. Appl. No. 13/749,038."
Office action dated Oct. 4, 2012 for U.S. Appl. No. 12/776,225.
Office action dated Oct. 23, 2014 for U.S. Appl. No. 14/015,934.
Office Action dated Nov. 28, 2017 for U.S. Appl. No. 14/585,654.
Office action dated Dec. 4, 2015 for U.S. Appl. No. 13/855,445.
Office action dated Dec. 5, 2014 for U.S. Appl. No. 13/692,596.
Ogose et al., "Histological Assessment in Graft of Highly Purified Beta-Tricalcium Phosphate (Osferion) in Human Bones," Biomaterials. Mar. 2006;27(8):1542-1549.
Ogose et al., "Histological Examination of 6-Tricalcium Phosphate Graft in Human Femur," J Biomed Mater Res, 2002;63(5):601-604.
Parcus Medical, LLC, "Parous V-LoxTM PEEK CF Suture Anchor", pp. 15, 16 of 510(k) Summary, FDA Approval Letter and Indications of Use for 510(k) No. K091094, Sep. 2009, 5 pages total.

(56) References Cited

OTHER PUBLICATIONS

Parcus Medical, LLC, "PEEK CF V-LoxTM Suture Anchor Demo" [video]; can be view at:<http://www.parcusmedical.com/techniques/animations/peek-vlox-anchor-demo.html>.
Parcus Medical, LLC, "V-LoxTM PEEK CF Suture Anchor [Production Information and Directions for use", undated, 2 pages total.
Parcus Medical, LLC, "V-LoxTM PEEK CF Suture Anchors Product Information Sheet" [brochure] undated, 1 page total.
Parcus Medical, LLC, "V-LoxTM PEEK CF Suture Anchors" [website]; retrieved from the Internets http://www.parcusmedical.com/products/peek-anchor.html>, 2 pages total.
Park et al., "Transosseous-Equivalent Rotator Cuff Repair Technique," Arthroscopy, Dec. 2006; 22(12):1360.e1-1360.e5.
Romeo et al., "Arthroscopic Repair of Full-Thickness Rotator Cuff Tears: Surgical Technique and Instrumentation" Orthopedic Special Edition, 2001; 7(1 of 2):25-30; retrieved from the Internet:< http://www.cartilagedoc.org/downloads/shoulder/Rotat.pdf>.
Schamblin, Conexa® Case Series Report: Arthroscopic Reinforcement of Revision Rotator Cuff Repair Tornier, Inc., 2009, 2 pages; retrieved from the Internets www.bhportho.com/docs/Conexa_RCR_Repair_Schamblin.pdf>.
Smith & Nephew, Inc., "2008 Product Catalog" [catalog], 2009, 311 pages total.
Smith & Nephew, Inc., "2009 Product Catalog" [catalog], 2008, 373 pages total.
Smith & Nephew, Inc., "ACCU-PASS Suture Shuttle" [video animation] 2005, 59 image screen shots; can be view at :< http://endo.smith-nephew.com/fr/View.asp?guid={6F27C42E-1632-4974-84E9-F18922FC19AA}&b=2->.
Smith & Nephew, Inc., Bioraptor 2.9 Suture Anchor [video animation], 2004; can be viewed at:< http://endo.smith-nephew.com/fr/View.asp?guid={98BCCE86-B5C2-413F-80AE¬CF7260A38C17}&b=2-BIORAPTOR%20animation.wmv>.
Smith & Nephew, Inc., "Bioraptor 2.9" [website], 3 pages total; retrieved from the Internet:<http://endo.smith-nephew.com/fr/node.asp?NodeId=3608>.
Smith & Nephew, Inc., "Bioraptor PK suture Anchor", 510(k) Summary, FDA Approval Letter, and Indications of Use for 510(k) No. K071586, Aug. 2007, 5 pages total.
Smith & Nephew, Inc., "ELITE PASS Premium Arthroscopic Suture Shuttle" [video animation], Mar. 2005, 44 image screen shots; video can be viewed at:< http://global.smith-nephew.com/US/showfile.XML?doc=V1- ELITE_PASS_Animation(26)_.wmv>.
Smith & Nephew, Inc., "FOOTPRINT PK Suture Anchor: Arthroscopic Shoulder Repair Using the Smith & Nephew FOOTPRINT PK Suture Anchor" [brochure], 2008, 12 pages total.
Smith & Nephew, Inc., "Kinsa Suture Achnor" [website], 2 pages; retrieved from the Internet:< http://www.endo.smith-nephew.com/fr/node.asp?NodeId=3739>.
Smith & Nephew, Inc., "OsteoraptorTM Suture Anchor", pp. 10-11 of 510(k) Summary, FDA Approval Letter, and Indications of Use for 510(k) No. K082215, Nov. 2008, 5 pages total.
Smith & Nephew, Inc., "TWINFIX Suture Anchors with ULTRABRAID Suture—Unparalleled strength, superior handling" [brochure], 2005, 12 pages total.
Smithnephew. Shoulder Series Technique Guide: Arthroscopic Shoulder Repair Using the Smith & Nephew Kinsa Suture Anchor [brochure], Smith & Nephew, Inc., Sep. 2006, Rev. B, 12 pages total; retrieved from the Internet: http://global.smithnephew.com/cps/rde/xbcr/smithnephewls/V1-10600180b%2829%29.pdf.
Spiralok and -Bio-Corkscrew FT Cadaver Study [white paper], no publication information, 2 pages total.
Stryker Corporation, "Shoulder Repair Made Simpler: Champion Shoulder Instrumentation" [brochure], 2008, 4 pages total.
Stryker Corporation, One Shot for Success—Titanium Wedge Anchor [brochure], 2008, 4 pages total.

Stryker Corporation, "PEEK TwinLoop" [website], 1 page; retrieved from the Internet: http://www.strykercom/enus/products/Orthopaedics/SportsMedicine/ShoulderInstrumentation/Anchors/Peek/056652.
Stryker Corporation, "Point to the Solution: BioZip Absorbable Suture Anchor" [brochure,] 2008, 4 pages total.
Stryker Corporation, Strength & Flexibility in Soft-Tissue Repair [brochure], 2008, 4 pages total.
Stryker Corporation, Stronger Than Ever: PEEK Zip Anchor [brochure] 2008, 4 pages total.
Stryker Corporation, "Suture Sliding Made Simple" [brochure], 2005, 4 pages total.
Stryker. Stability, Precision, Flexibility—PEEK Twinloop Anchor [brochure], Stryker Corporation, Jun. 2008, Rev 1,4 pages total; retrieved from the Internets http://www.strykercom/stellent/groups/public/documents/web_prod/056750.pdf>.
Tetik et al., "Bioabsorbable Interference Screw Fixation in a Bone Tunnel: Comparison of 28mm; 35 \mm Single Screw Fixation and Bi-Cortical Fixation with a 20mm and 17mm Screws," Lexington, Kentucky, undated, 3 pages total.
Tornier, Inc., "CinchTM Knotless Fixation Implant System", pp. 38-40 of 510(k) Summary, FDA Approval Letter and Indications of Use for 510(k) No. K080335 , Feb. 2008, 6 pages total.
Tornier, Inc., "InsiteTM Suture Anchors", pp. 66-67 of 510(k) Summary, FDA Approval Letter and Indications of Use for 510(k) No. K080368, Feb. 2009, 5 pages total.
Tornier. Piton Knotless Fixation System, Tornier, Inc., 2009, 3 pages total; retrieved from the Internets http://www.tornier-US.com/sportsmed/smd003/index.php?pop=1> on Oct. 14, 2009.
U.S. Appl. No. 13/692,596, filed Dec. 3, 2012.
U.S. Appl. No. 13/749,038, filed Jan. 24, 2013.
U.S. Appl. No. 13/855,445, filed Apr. 2, 2013.
U.S. Appl. No. 14/015,934, filed Aug. 30, 2013.
U.S. Appl. No. 14/585,654, filed Dec. 30, 2014.
U.S. Appl. No. 14/804,178, filed Jul. 20, 2015.
Vogt et al., "Injuries to the Articular Cartilage," European Journal of Trauma, Aug. 2006; 32(4):325-331.
Walsh et al., "Healing of A Critical Size Defect In Sheep Using Bone Graft Substitutes in Block Form," Poster No. 1433, 53rd Annual Meeting of the Orthopaedic Research Society, San Diego Convention Center, San Diego, California, Feb. 11-14, 2007, 1 page total.
Warden et al., "Magnetic Resonance Imaging of Bioabsorbably Polylactic Acid Interference Screws During the First 2 Years After Anterior Cruciate Ligament Reconstruction," Arthroscopy, July-August, 15(5):474-480.
Weiler et al., "Biodegradable Implants in Sports Medicine: The Biological Base," Arthroscopy, Apr. 2000;16(3):305-321.
Yanke et al., 'Arthroscopic Double-Row and "Transosseous-Equivalent" Rotator Cuff Repair,' Am J Orthop (Belle Mead NJ). Jun. 2007;36(6):294-297.
Zimmer, Inc., "Labral Repair with Statak Suture Anchors—Surgical Techniques: Arthroscopic & Open" [brochure], 1996, 6 pages total.
Zimmer, Inc., "Rotator Cuff Repair with Statak Suture Anchors—Surgical Techniques: Arthroscopic & Open" [brochure], 1996, 6 pages total.
Office action dated Nov. 1, 2019 for U.S. Appl. No. 15/361,850.
U.S. Appl. No. 14/585,654 Notice of Allowance dated Oct. 18, 2019.
U.S. Appl. No. 14/804,178 Notice of Allowance dated Jul. 2, 2019.
U.S. Appl. No. 14/804,178 Notice of Allowance dated Jul. 9, 2019.
U.S. Appl. No. 14/804,178 Notice of Allowance dated Mar. 27, 2019.
U.S. Appl. No. 15/190,332 Notice of Allowance dated Nov. 7, 2019.
U.S. Appl. No. 14/585,654 Notice of Allowance dated Jan. 28, 2020.
U.S. Appl. No. 15/190,332 Notice of Allowance dated Jan. 30, 2020.
U.S. Appl. No. 15/361,850 Notice of Allowance dated Jan. 29, 2021.
U.S. Appl. No. 15/361,850 Notice of Allowance dated Mar. 31, 2021.
U.S. Appl. No. 15/361,850 Office Action dated Jul. 21, 2020.

* cited by examiner

METHODS AND DEVICES FOR SUTURE ANCHOR DELIVERY

CROSS-REFERENCES TO RELATED APPLICATIONS

The present application is a continuation of U.S. patent application Ser. No. 14/804,178, filed Jul. 20, 2015, which is a divisional of U.S. patent application Ser. No. 13/692,596, filed Dec. 3, 2012, which is a continuation of U.S. patent application Ser. No. 12/605,065, filed Oct. 23, 2009, which is a non-provisional of, and claims the benefit of priority of U.S. Provisional Patent Application No. 61/108,420, filed Oct. 24, 2008; the entire contents of which are incorporated herein by reference.

BACKGROUND OF THE INVENTION

1. Field of the Invention

The present disclosure relates to medical devices, systems and methods, and more specifically to methods, systems and devices used for anchoring suture and delivery of suture anchors.

Soft tissue such as tendons, ligaments and cartilage are generally attached to bone by small collagenous fibers which are strong, but which nevertheless still can tear due to wear or disease. Examples of musculoskeletal disease include a torn rotator cuff as well as a torn labrum in the acetabular rim of a hip joint or the glenoid rim in a shoulder joint.

Thus, treatment of musculoskeletal disease may involve reattachment of torn ligaments, tendons or other tissue to bone. This may require the placement of suture anchors in the humeral head for reattachment of a torn rotator cuff, placement of suture anchors in the acetabular or glenoid rim for reattachment of the torn labrum, placement of tacks to attach labral tissue to the glenoid rim, placement of screws in the vertebral bodies to attach cervical plates for spinal fusion, placement of screws in small joint bones for stabilizing reduced fractures, etc. A suture anchor is a device which allows a suture to be attached to tissue such as bone. Suture anchors may include screws or other tubular fasteners which are inserted into the bone and anchored in place. After insertion of the anchor, the tissue to be repaired is captured by a suture, the suture is attached to the anchor (if not already pre-attached), tension is adjusted, and then the suture is often knotted so that the tissue is secured in a desired position.

Delivery of a suture anchor to a treatment site can be time consuming and challenging to undertake in the tight space encountered during endoscopic surgery and sometimes even in conventional open surgery. In most surgical procedures, a pilot hole is drilled at the implantation site prior to screwing in the device. In other cases a self-tapping device tip is used to screw in the device without a pilot hole. Alternatively, ultrasonic energy has been proposed in embedding bone anchors in bony tissue without pre-drilling a pilot hole. These methods of implanting a device in bone tissue, while commonly used in surgery today, are not optimal. Pre-drilling a pilot hole prior to placing the device requires the surgeon to exchange tools through the cannula and to locate the pilot hole after introducing the implant in the arthroscopic field. Self-tapping devices are limited to use at sites with the appropriate thickness of cortical bone. Ultrasonic energy based devices are susceptible to large energy losses with minor changes in device configuration, and rely on ultrasonic energy sources which can be expensive. It would therefore be desirable to provide a suture anchor system that provides easy access to the treatment site and that can easily and accurately deliver a suture anchor to a desired location.

In a particular application, treating musculoskeletal disease in a hip joint can be especially challenging. The hip joint is a deep joint surrounded by a blanket of ligaments and tendons that cover the joint, forming a sealed capsule. The capsule is very tight thereby making it difficult to advance surgical instruments past the capsule into the joint space. Also, because the hip joint is a deep joint, delivery of surgical instruments far into the joint space while still allowing control of the working portions of the instrument from outside the body can be challenging. Additionally, the working space in the joint itself is very small and thus there is little room for repairing the joint, such as when reattaching a torn labrum to the acetabular rim. Thus, the suture anchor tool must be small enough to fit in the limited space. Moreover, when treating a torn labrum, the suture anchor must be small enough to be inserted into the healthy rim of bone with adequate purchase, and the anchor also must be short enough so that it does not protrude through the bone into the articular surface of the joint (e.g. the acetabulum). Thus, the anchor delivery instrument must also be able to hold and deliver suture anchors having a small diameter and small length.

Therefore, it would be desirable to provide improved suture anchors and suture anchor delivery instruments that overcome some of the aforementioned challenges. Such suture anchors and delivery instruments are preferably suited to arthroscopic procedures, and in particular labral repair in the hip. At least some of these objectives will be met by the disclosure described below.

2. Description of the Background Art

Patents disclosing suture anchoring devices and related technologies include U.S. Pat. Nos. 7,566,339; 7,390,329; 7,309,337; 7,144,415; 7,083,638; 6,986,781; 6,855,157; 6,770,076; 6,767,037; 6,656,183; 6,652,561; 6,066,160; 6,045,574; 5,810,848; 5,728,136; 5,702,397; 5,683,419; 5,647,874; 5,630,824; 5,601,557; 5,584,835; 5,569,306; 5,520,700; 5,486,197; 5,464,427; 5,417,691; and 5,383,905. Patent publications disclosing such devices include U.S. Patent Publication Nos. 2009/0069845; 2008/0188854; and 2008/0054814.

BRIEF SUMMARY OF THE INVENTION

The current invention comprises surgical devices and methods to treat various soft tissue and joint diseases, and more specifically relates to suture anchors and suture anchor delivery instruments used in the treatment of bone, cartilage, muscle, ligament, tendon and other musculoskeletal structures.

In a first aspect of the present invention, a method for impacting a suture anchor into bone comprises providing an implantable suture anchor, and providing an impactor device for impacting the suture anchor into the bone. The suture anchor is coupled to a distal portion of the impactor device. Positioning the suture anchor engages the suture anchor with the bone at an implantation site, and powering the impactor device impacts the suture anchor thereby implanting the suture anchor into the bone. The frequency of impaction is less than 20 KHz. The impactor device is decoupled from the suture anchor and then the impactor device is removed from the implantation site.

The suture anchor may pass through adjacent musculoskeletal tissues and may attach the adjacent musculoskeletal tissues to the bone. The adjacent musculoskeletal tissues may comprise bony tissues or soft tissues. The suture anchor may include one or more lengths of suture. Powering of the impactor device may comprise pneumatically, electrically, mechanically, or magnetically actuating the impactor device. The impactor device may impact the anchor when powered so as to linearly, rotationally, or linearly and rotationally drive the suture anchor into the bone. The frequency of impaction may be less than 1 KHz. The impaction may have an amplitude of 1,000 micrometers or less per impact.

The method may further comprise expanding a portion of the suture anchor radially outward so as to firmly engage the suture anchor with the bone. The suture anchor may comprise a plurality of fingers, and expanding a portion of the suture anchor may comprise releasing a constraint from the fingers so as to allow the fingers to radially expand outward. The impactor device may comprise an elongate tubular shaft and the step of decoupling may comprise advancing the suture anchor axially away from a distal portion of the shaft. The method may also comprise cooling the suture anchor or the implantation site with a fluid.

In another aspect of the present invention, a suture anchor delivery system comprises an implantable suture anchor having a longitudinal axis and a plurality of fingers circumferentially disposed therearound. The fingers have a constrained configuration and an unconstrained configuration. In the constrained configuration the fingers are substantially parallel with the longitudinal axis, and in the unconstrained configuration, the fingers expand radially outward. The system also includes an impactor device for impacting the suture anchor into bone. The suture anchor is releasably coupled to a distal portion of the impactor device.

In a further aspect, the invention provides a suture anchor formed of shape memory material and having an unbiased configuration adapted to securely fix the anchor in bone or other tissue. The suture anchor is deformable into a configuration adapted for delivery into the bone or tissue, from which it may be released so that it returns toward its unbiased configuration thereby anchoring the anchor in the bone or tissue. In various embodiments, the anchor may have in its unbiased configuration a plurality of resilient fingers that extend radially outward, a curved shape formed around a transverse axis, two or more wings that flare outwardly in the proximal direction, or two or more longitudinal divisions defining a plurality of axial elements that bow or deflect outwardly. Other structures are disclosed herein.

In another aspect, the invention provides a suture anchor having a tapered tip adapted for being driven into bone, with or without a pre-drilled hole, a shaft extending proximally from the tip, and a means for attaching a suture to the shaft. The tip, the shaft, or both are cross-shaped in cross section.

The suture anchor may comprise a textured outer surface to allow for bone ingrowth. The suture anchor may also comprise a length of suture coupled thereto. The impactor device may impact the suture anchor at a frequency of less than 20 KHz, or at a frequency of less than 1 KHz. the impactor device may comprise an actuation mechanism for impacting the suture anchor that is pneumatically, electrically, magnetically, or mechanically actuated. The impactor device may impact the suture anchor and drive the anchor into the bone or other tissue in a linear, rotational, or linear and rotational manner. The impactor device may impact the suture anchor with an impaction having an amplitude of 1,000 micrometers or less per impact. The system may further comprise a cooling system for cooling the impactor device and suture anchor during impaction. The cooling system may comprise a cooling fluid.

These and other embodiments are described in further detail in the following description related to the appended drawing figures.

DETAILED DESCRIPTION OF THE INVENTION

The devices and methods disclosed herein address at least some of the limitations of current methods of implanting devices into bony tissue. The method involves driving the device into bony tissue by impaction whereby, an impactor drives the implant into bone at frequencies between 10 and 20 KHz, preferably between 20 and 1000 Hz, most preferably between 30 and 500 Hz; and at amplitudes of 100 to 1000μ, preferably 200-750μ, most preferably 300-500μ. The implantable device may be loaded into the distal end of the impactor such that the distal end of the impactor and the attached device may be introduced into an arthroscopic field through a cannula.

Figure 1:
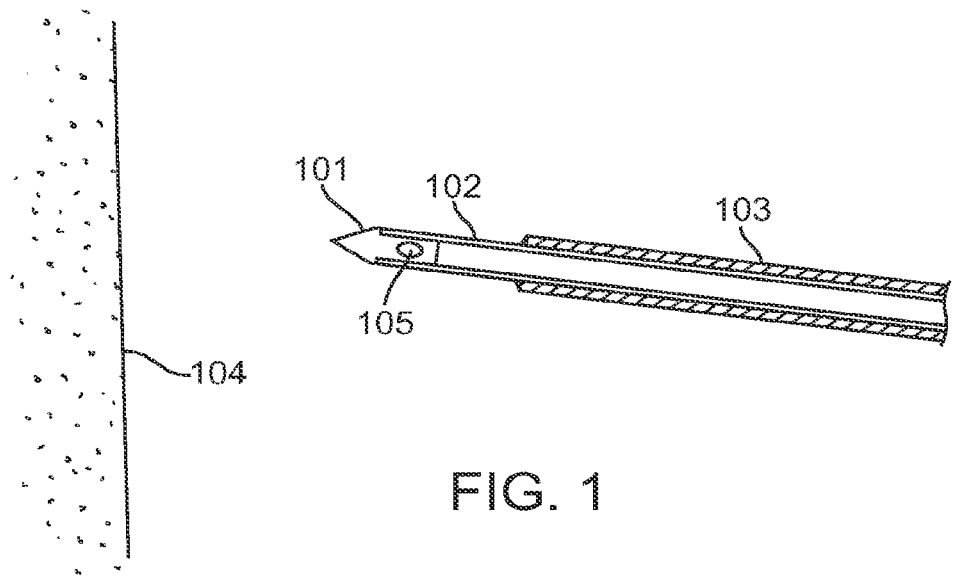
FIG. 1 is a sectional view of an anchor loaded in the distal end of an anchor driver and placed through a cannula.

FIG. 1, shows a sectional view of implant 103 loaded into an impactor 102 and introduced through a cannula 103. Implant 101 is located at the distal end of impactor assembly 102. The assembly 102 is introduced down the bore of cannula 103 and placed in the proximity of bony structure 104. Having been placed at the surface of bony structure 104 the impactor 102 is energized and the implant 101 is driven into the bone. Channel 105 extends transversely through the implant 103 and allows a suture to be secured thereto. During the impaction period, contact between the tip of the device and the bony tissue is maintained manually by the surgeon.

Figure 2:
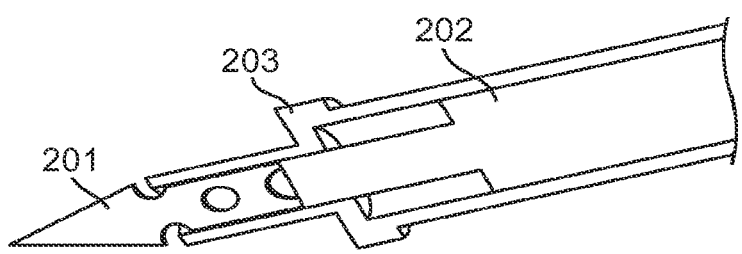
FIG. 2 is a sectional view of a flat anchor loaded into the distal end of an anchor driver with a stabilization sleeve.

In one exemplary embodiment the implant is impacted into the bone by application of force onto the proximal surface of the implant. Referring to FIG. 2, implant 201 is impacted by impactor member 202. This allows the implant 201 to be constructed with substantially consistent cross sections. Sleeve 203 can move relative to the implant 201 and impactor member 202 while remaining concentric and serves to stabilize and guide the implant 201 while the implant 201 is being impacted into the bone.

Figure 3:
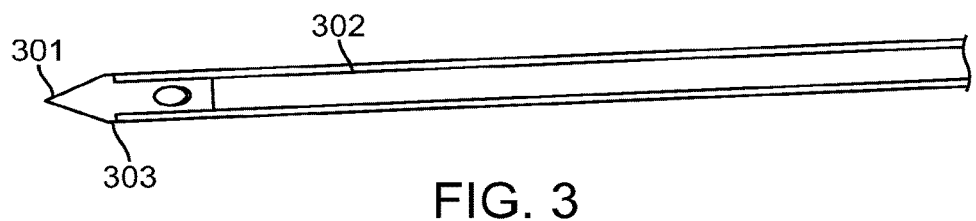
FIG. 3 is a sectional view of a round anchor loaded into the distal end of an anchor driver with a tubular profile.

In another embodiment the implant is configured with a stepped shoulder region 303 along the length of the body suitable for applying impaction force. FIG. 3 shows a cross sectional view of anchor 301 which has a round cross section and interfaces with the distal end of the impactor 302. The distal end of the impactor 302 is generally round and hollow. The distal end of the impactor 302 which interfaces with the anchor device 301 could be of varying length to enable introduction through cannulas used to access joint spaces in the shoulder, knee, hip etc. The impactor 302 may also be loaded with multiple devices.

At the frequencies utilized during deployment of anchors, the amount of energy loss by heat dissipation is low. However, the distal end of the impactor may optionally be designed to circulate cold fluid to regulate the temperature of the impactor tip and the implant. Other forms of cooling well know in the art may also be used in conjunction with the impactor.

The frequency and amplitude of the impactor may be adjusted to optimize the implantation process depending on the size of the implant, the design of the implant, as well as the properties of bone at the implant site, etc.

Figure 4:
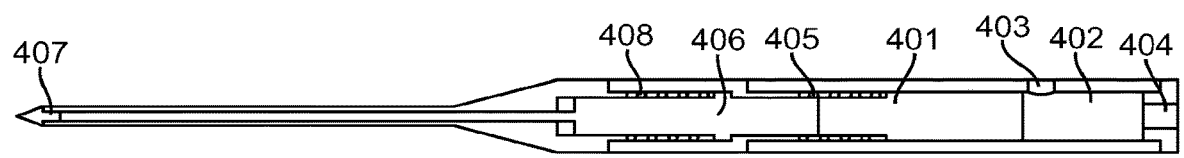
FIG. 4 is a sectional view of the body of a pneumatic powered impactor.

In another embodiment, the impactor is powered by compressed gas which is commonly available in operating rooms. FIG. 4 shows a cutaway view of one embodiment of a pneumatic driver used for placing devices in bony tissue. Shuttle element 401 is cycled back and forth based on air pressure by selectively pressurizing and releasing pressure in chamber 402 through the cyclic motion of shuttle 401 relative to ports 403 and 404. As the shuttle moves port 403 is selectively covered or uncovered causing the shuttle to reverse direction based on the action of spring 405 which rebounds shuttle 401 back into the depressurized chamber 402. At one end of the shuttle travel, the shuttle impacts active element 406 which is in contact with the proximal end of the device 407 thereby transmitting the energy from the shuttle 401 to the device 407 with each cycle. At the end of the cycle, the spring 408 returns the active element 406 back to its original position. Those skilled in the art will appreciate that the system shown in FIG. 4 is an exemplary system and the same effect could be accomplished with a variety of pressured driving mechanisms.

Figure 5:
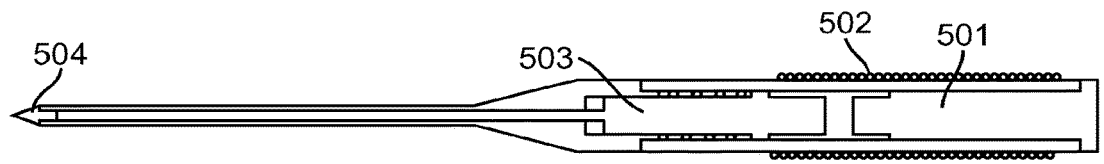
FIG. 5 is a sectional view of the body of a electromechanically powered impactor.

In another embodiment, the impactor could be designed to operate using a mechanical shuttle mechanism driven by an electromagnetic field. FIG. 5 shows a sectional view of an instrument used for driving devices into bony tissue. Shuttle element 501 may be composed of any ferromagnetic material and is cycled back and forth based on the magnetic field created by a coil 502 which is connected to a signal generator capable of generating alternating current. At one end of the shuttle travel, the shuttle impacts active element 503 which is in contact with the proximal end of the device 504 thereby transmitting the energy from the shuttle to the device with each cycle. Those skilled in the art will appreciate this system shown in FIG. 5 is an exemplary system and the same effect could be accomplished with a variety of electromechanical driving mechanisms.

Figure 6:
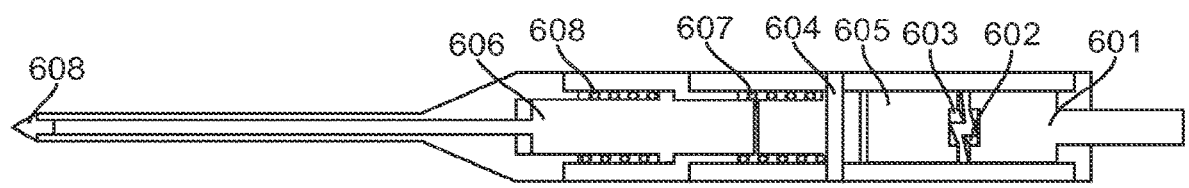
FIG. 6 is a sectional view of the body of an impactor with a rotary mechanism.

In another embodiment, the impactor could be designed to operate using mechanical means whereby rotary motion is converted to linear motion. FIG. 6 shows a sectional view of an instrument used for driving devices into bony tissue. Cable driven cam 601 is designed with a circular ramp 602 that interfaces with mating ramp 603 that is part of shuttle 605 that does not rotate due to pin 604 and slot in 603. Rotation of ramp 602 causes mating ramp 603 to move in a reciprocating fashion which is transmitted to the active element 606 which in turn imparts its energy to implant 608. Shuttle 605 returns to its original position once ramps 602 and 603 have disengaged via the force applied by spring 607. This allows active element 606 to return due to the force applied by spring 608. Those skilled in the art will appreciate this system shown in FIG. 6 is an exemplary system and the same effect could be accomplished with a variety of mechanisms that convert rotational motion into reciprocating motion.

In all the embodiments described above, by altering the pressure, current, rotational speed etc., the frequency and amplitude of the impactor can be varied to enable the surgeon to select settings that are appropriate for various tissue properties (e.g.; cortical bone, cancellous bone, etc.)

Figure 7:
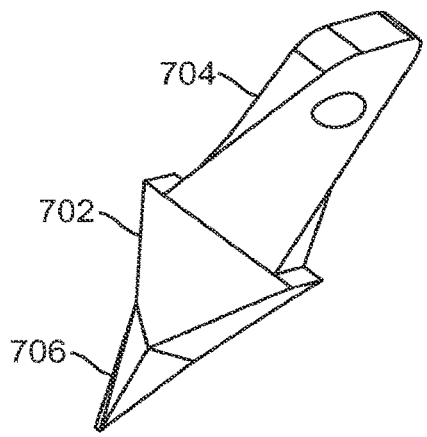
FIG. 7 is an example of an anchor.

In addition to the embodiments described above, the impactor may have linear and rotational motion combined to create a reciprocating twisting motion. By creating a reciprocating twisting motion, devices may be driven in more securely into bony tissue, thereby increasing the stability of the implanted device. The amount of twisting motion may be varied based on the specific design and dimensions of the device. FIG. 7 illustrates an exemplary embodiment of a suture anchor device 702 having a pointed distal tip 706 and a main shaft 704. Both the main shaft 704 and the distal tip 706 have a twisted, helical-like configuration so that the anchor will rotate as it is being driven into the bone by an impactor having a reciprocating twisting motion.

Figure 8A:
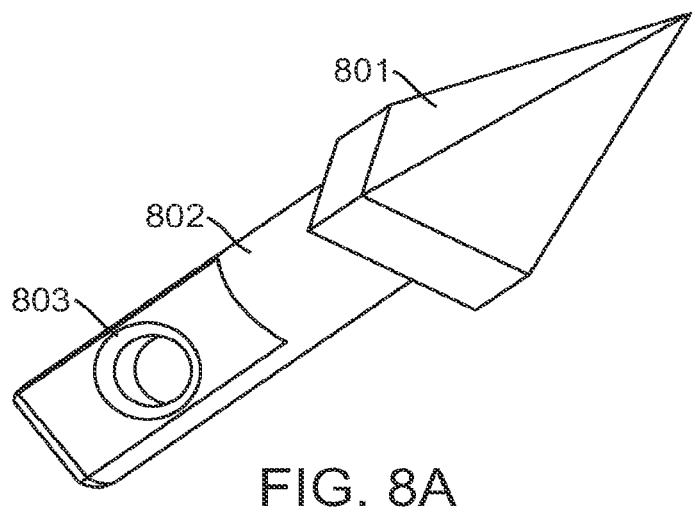
FIGS. 8A-8D are examples of anchors.
Figure 8B:
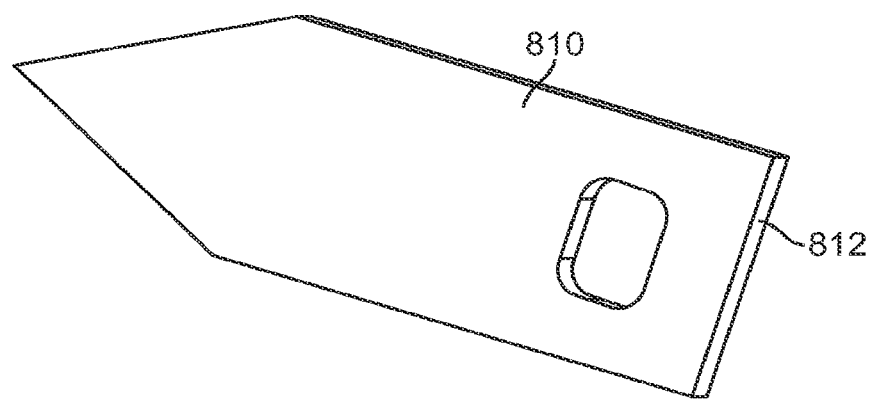
Figure 8C:
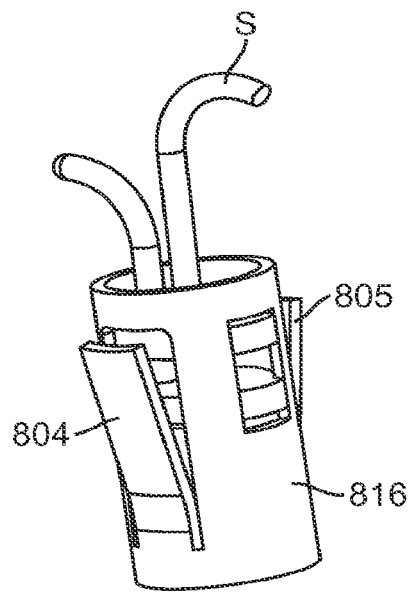
Figure 8D:
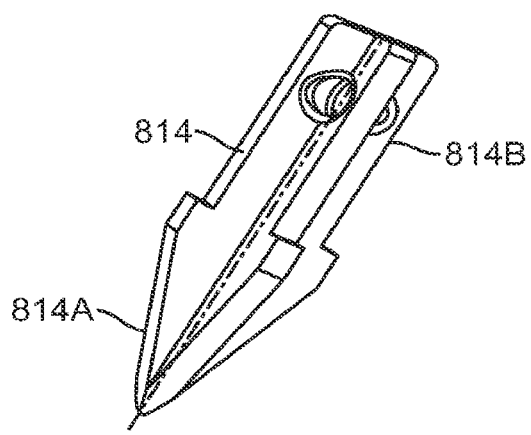

The impaction method has advantages that are not limited to a particular device design. For example, the implant may be cylindrical, flat, or a have a variety of other cross sections. Additionally the cross section may change along the length of the implant. FIGS. 8A-8D show a variety of anchor devices that may be useful in this application. The implant may be threaded or plain. FIG. 8A shows an anchor with a tip 801 which has a triangular pointed tip while the shank 802 has a substantially round cross section. Shank 802 has a hole 803 that passes through the shank allowing for attachment of a suture. FIG. 8B shows an anchor 810 having a rectangular cross section 812 resulting in a generally flat configuration. FIG. 8C shows an anchor 816 with a cross section generally described as a hollow tube and a suture S coupled thereto. In the embodiment shown in FIG. 8C, wings or fingers 804 and 805 are active elements that deploy once the implant is released from the delivery instrument. For example wings or fingers 804, 805 may be fabricated from a superelastic material like Nitinol, spring temper stainless steel, a resilient polymer, or the wings may be fabricated from a shape memory alloy, such that once the anchor 816 is advanced from the delivery instrument and the wings 804, 805 become unconstrained, they spring open, radially outward. The wings help secure the anchor 816 into bone or other tissue. In alternative embodiments, the wings 804, 805 may be deformed into the flared radially outward position to help secure the anchor into the bone. For example, a plunger may be advanced into the center of the anchor thereby causing the wings 804, 805 to flare outward. FIG. 8D shows an anchor 814 with a tip 814A and a shank 814B having a generally X-shaped or cross-shaped cross section that may inserted into bone using the techniques described herein. In the embodiment shown, both the tip and the shank of anchor 814 have a cross-shape cross-section, although in other embodiments just the tip or just the shank may have a cross-shape. Shank 814B has a transverse hole through which a suture may be threaded. Other means of attachment of the suture to the shank may also be used.

Figure 9A:
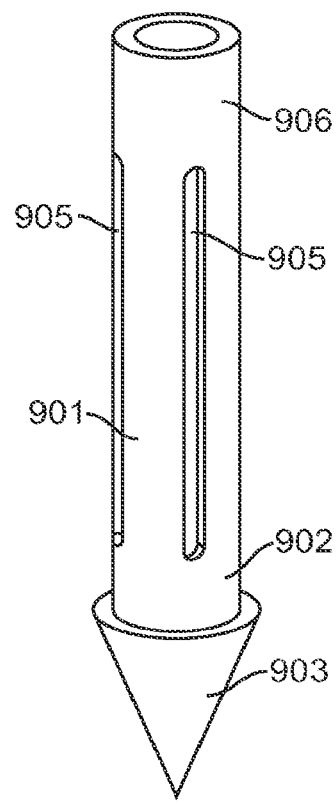
FIGS. 9A-9B are examples of anchor in a constrained and deployed configuration.
Figure 9B:
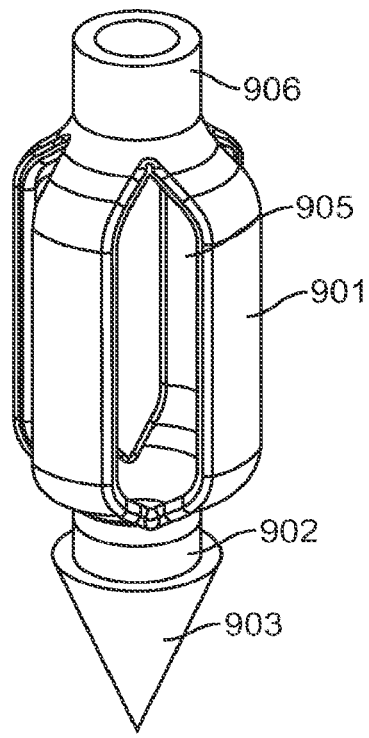

Additionally, the implant and driver could be designed such that a loaded implant constrained by the driver is placed at the implantation site. Following placement, the implant recovers to a pre-determined shape that enhances the anchoring of the implant in the bony tissue. FIG. 9A shows a cylindrically shaped tubular expandable anchor 906 in its loaded (constrained) condition. The anchor comprises a plurality of axially oriented slits 905 that form a plurality of axially oriented elements 901. Element 901 is an active element that can be constrained to the profile of the non active portion of the implant 902. Element 901 is replicated in a circular pattern around the periphery of the implant 906. Conically shaped nosecone 903 is distal to the end of the driver instrument (not illustrated) while the shank is composed of active elements and non active portions 901 and 902 respectively. The anchor 906 is constrained in the delivery instrument. FIG. 9B shows the same anchor 906 in its deployed configuration after being released and unconstrained from the delivery instrument (not illustrated). Elements 901 are self-expanding and thus have moved to an expanded position to lock the anchor into the bony tissue. The elements 901 may be fabricated from self-expanding materials such as superelastic nitinol, shape memory alloys, spring temper metals, resilient polymers, or other resilient materials. Expansion element 901 causes a shortening of the overall anchor 906 length. In the case where there is a preloaded suture or soft tissue fixation element attached to 901, this shortening of the anchoring element can be used as a tensioning means for the soft tissue fixation element. Tensioning the soft tissue fixation would provide improved coaptation of the soft tissue to the bone, and improve the repair. The degree of foreshortening can be programmed into the device by modifying one or a combination of the diameter of the distal driving (pointed) element of 901, the length of the shaft of 901, the diameter of the shaft of 901, and the specific design of the cutouts 905 of 901.

Change in the implant after implantation could be based on the expansion of the body of the anchor as shown in FIG. 9B or by deployment of a fixation member from the body of the anchor as shown in FIG. 8C. A combination of the expansion of the body of the anchor and deployment of members from the body could also be used. Expansion of the anchor could include mechanical means of expanding the anchor from a first configuration to a second configuration based on the malleability of the material or could be achieved through the use of self-expanding or shape memory materials. Deployment of fixation members may be achieved through various means including shape memory and mechanical means. The implants may include one or more sutures. The body of the implant may have holes to allow for bony in-growth into or across the implant. The surface of the implant may be textured or porous to allow for bone in-growth to enhance long term anchoring of the implant. The implant may be hollow to allow for bony in-growth within the implant. An advantage of using a hollow implant is the entrapment of the bone particles from the implantation site within the implant during impaction.

Figure 10A:
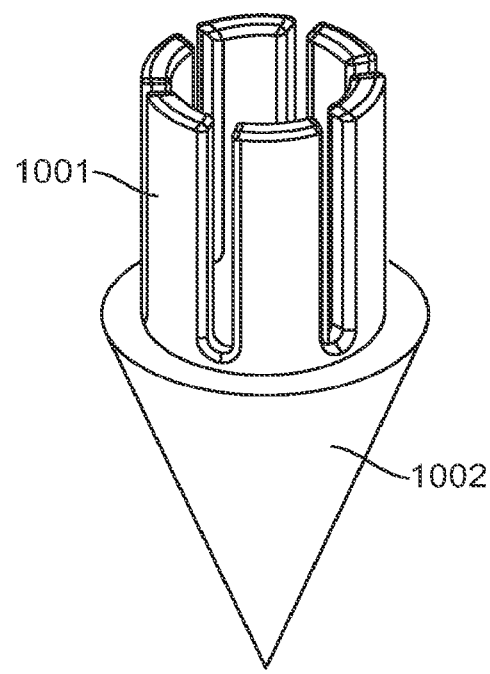
FIGS. 10A-10B are examples of a device for sutureless attachment of tissue to bone in a constrained and deployed configuration.
Figure 10B:
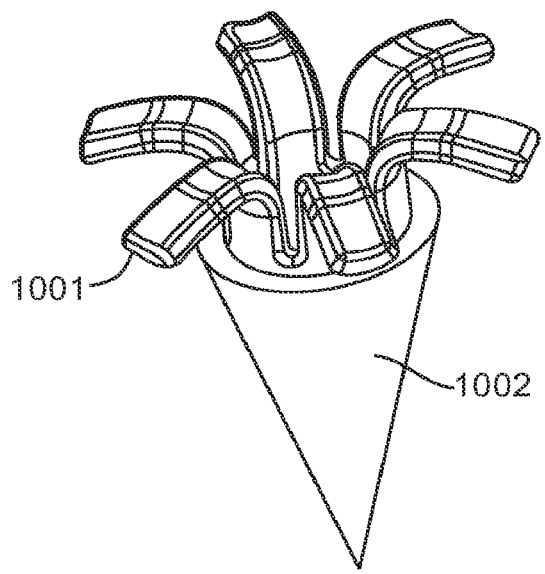

An additional embodiment of the current invention is an anchor configured to provide for fixation of tissue directly to the bone adjacent to the anchor location. FIG. 10A shows the anchor in a constrained configuration for delivery. Active elements 1001 are constrained in this undeployed state in the distal end of the driver (not illustrated) while nosecone 1002 may be exposed beyond the distal end of the driver. FIG. 10B shows the same anchor after it has been placed in bony tissue and the anchor has been deployed from the delivery instrument so that it is unconstrained. Active elements 1001 include a plurality of fingers that are axially aligned with the longitudinal axis of the anchor when constrained, and expand radially outward when unconstrained. The elements spread out and allow for the capture of tissue between the fingers and the bone or other tissue into which the anchor is disposed. Nosecone 1002 is affixed into bony tissue. By varying different parameters of element 1001 which may include but are not limited to the thickness, material, heat treating, and radius of curvature of the deployed device, it will be possible to change the force of apposition between the two tissues to be fixed. This design also provides a degree of self-adjustment, allowing different tissue thicknesses to be attached to underlying bone by a single device without requiring a suture. By having a radius of curvature which changes along the length of the active elements 1001 rather than a constant radius of curvature, the device can be programmed to provide approximately the same force of apposition for a range of tissue thicknesses to the underlying bone with the same device design. This allows a surgeon to use a single cartridge-loaded device to place a number of anchors without device exchange.

Element 1001 may be made from a resorbable material such as PLLA, collagen, highly crosslinked hyaluronic acid or the like. While some of these materials may be processed and formed to self-deploy as described above, many require secondary steps after placement to deform them into a fixation shape. As an example, when element 1001 is made from PLLA, a secondary step may include application of heat to element 1001 to plastically deform it into the desired final configuration. Once the heat source is removed, the PLLA or other plastically deformable material remains in its final shape and position. In other embodiments, the elements 1001 may be fabricated from self-expanding material like nitinol, spring temper metals, or resilient polymers. The elements may also be made from shape memory materials including metal alloys like nitinol or shape memory polymers.

Additionally, elements 1001 and 1002 may be two separate elements, with element 1001 being placed on top of the tissue to be fixed, and 1002 being driven down through element 1001 and into the underlying bone, fixing element 1001 and tissue to be fixed. In this embodiment, element 1001 may be slotted as shown, or it may be configured more like a washer or grommet shape.

In another embodiment both the portion of the anchor located in bony tissue and the anchor portion in the adjacent tissue may be configured with both elements being active.

Figure 11A:
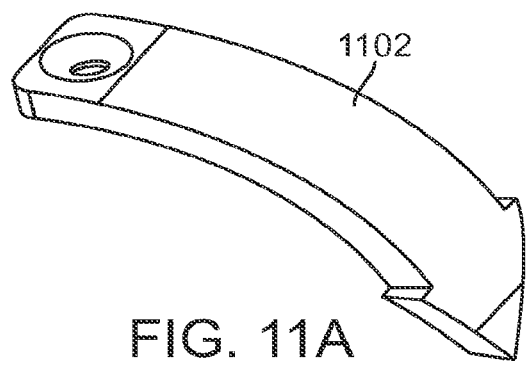
FIGS. 11A-11B are examples of a curved anchor in a constrained and deployed configuration.
Figure 11B:
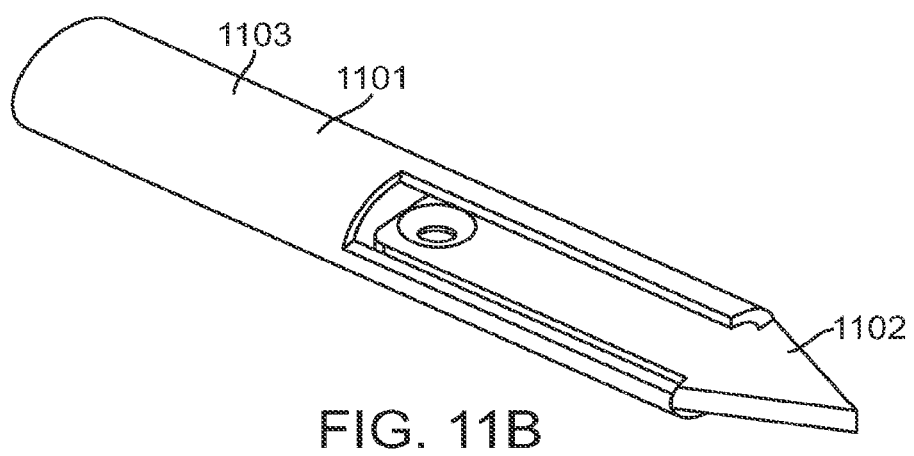

In yet another embodiment, an anchor 1102 may be constructed with a generally curved profile as shown in FIG. 11A. FIG. 11B shows the anchor 1102 once it is loaded into a delivery system 1103 which constrains it to a generally straight profile within a constraining sleeve 1101 that is part of the driver. As the anchor 1102 is deployed from the constraining sleeve 1101 into the bone, it advances along a curved profile into the implantation site.

The implants described in this invention could be made from metals like stainless steel, titanium, nitinol, etc., as well as resorbable and non-resorbable polymers like PLLA, PEEK etc. Implants may also be composites of two or more materials.

The method, devices and implants described above could be used in a variety of applications including any application that requires an implant to be anchored into bony tissue. For example, placement of bone anchors in the humeral head for reattachment of a torn rotator cuff, placement of bone anchors in the acetabular or glenoid rim for reattachment of the torn labrum, placement of tacks to attach labral tissue to the glenoid rim, placement of screws in the vertebral bodies to attach cervical plates for spinal fusion, placement of screws in small joint bones for stabilizing reduced fractures, for treating stress urinary incontinence with a bone-anchored pubovaginal sling, placement of plates in cranio-facial reconstruction, fixation of fractures, etc.

While the device and implants are designed to be used preferably in arthroscopic or minimally invasive procedures, they could also be utilized in open or mini-open surgical procedures.

The implants in this invention may be loaded into a delivery device (e.g. a tube) which can be attached to the distal end of the impactor. The loaded delivery device may be designed to be introduced through a standard arthroscopic cannula and may contain one or more implants, thereby enabling the implantation of multiple implants without removing the delivery tool from the arthroscopic field. The delivery device may have features like a slit to enable manipulation of sutures attached to the implant. Alternatively, the sutures may pass through the body of the delivery device and be accessible through the proximal end of the cannula.

Example 1

An impactor device was fabricated similar to the device shown in FIG. 4. Air pressure was used to cycle a metal shuttle that impacts the active member at the distal end of the impactor. A cylindrical anchor (proximal diameter=1.5 mm, body diameter=2 mm) with a conical distal tip (length of anchor=6 mm), was loaded into the distal tip of the impactor. A #2 braided polyester suture was attached to the anchor via a hole through the minor diameter of the anchor. The distal tip of the active member had an OD of 2 mm and ID of 1.5 mm, and a slit to allow for egress of the suture. The impactor anchor assembly was connected to 90 psi compressed air. The distal end of the assembly was placed in contact with fresh cadaveric bovine cortical and cancellous bone. An air supply valve was opened and the anchors were driven into the bony tissue with ease. The pullout strength of the anchors were assessed subjectively and indicated good fixation of the anchors. The anchors were then carved out of the bony tissue and the surrounding tissue was examined for gross damage. There was no sign of thermal necrosis or other damage at the implantation site.

While the above detailed description and figures are a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A system for impacting a suture anchor into bone, said system comprising:
    an implantable suture anchor configured to engage with the bone at an implantation site; and
    an impactor device for impacting the suture anchor into the bone, the impactor device having a movable impactor element, wherein the suture anchor is coupled to a distal portion of the impactor device;
    wherein, when actuated, the impactor device is configured to move the impactor element relative to the suture anchor in a plurality of cycles such that the impactor element impacts the suture anchor during each cycle to implant the suture anchor into the bone.

2. The system of claim 1, further comprising one or more lengths of suture coupled to the suture anchor.

3. The system of claim 1, wherein the impactor device comprises an actuation mechanism for impacting the suture anchor that is pneumatically actuated.

4. The system of claim 1, wherein the impactor device comprises an actuation mechanism for impacting the suture anchor that is electrically actuated.

5. The system of claim 1, wherein the impactor device comprises an actuation mechanism for impacting the suture anchor that is magnetically actuated.

6. The system of claim 1, wherein the impactor device comprises an actuation mechanism for impacting the suture anchor that is mechanically actuated.

7. The system of claim 1, wherein the impactor device impacts the suture anchor so as to linearly and rotatably drive the suture anchor into the bone.

8. The system of claim 1, wherein the impactor device impacts the suture anchor at a frequency of impaction of less than 1 KHz.

9. The system of claim 1, wherein the impactor device impacts the suture anchor at an amplitude of 1000 micrometers or less per impact.

10. The system of claim 1, wherein a portion of the suture anchor is configured to expand radially outward so as to firmly engage the suture anchor with the bone.

11. The system of claim 10, wherein the suture anchor comprises a plurality of fingers, and wherein the plurality of fingers are configured to radially expand outward when release from a constraint.

12. The system of claim 11, wherein the plurality of fingers are configured to be axially aligned with a longitudinal axis of the suture anchor when constrained with the constraint.

13. The system of claim 11, wherein the plurality of fingers are configured to capture tissue between the plurality of fingers and the bone when expanded radially outward.

14. The system of claim 1, wherein the impactor device comprises an elongate tubular shaft, and wherein the distal portion of the impactor device is configured to decouple from the suture anchor by advancing of the suture anchor axially away from a distal portion of the elongate tubular shaft.

15. The system of claim 1, further a cooling system for cooling the impactor device and the suture anchor during impaction.

16. The system of claim 1, wherein the impactor device impacts the suture anchor at a frequency of impaction of less than 20 KHz.

17. The system of claim 1, wherein the movable impactor element is disposed within a chamber of the impactor device, and wherein the impactor element is configured to move within the chamber relative to the suture anchor in the plurality of cycles when the impactor device is actuated.

* * * * *